(12) United States Patent
Goldstein

(10) Patent No.: US 8,859,201 B2
(45) Date of Patent: Oct. 14, 2014

(54) METHODS FOR SEQUENCING A BIOMOLECULE BY DETECTING RELATIVE POSITIONS OF HYBRIDIZED PROBES

(75) Inventor: Peter H. Goldstein, Boston, MA (US)

(73) Assignee: NABsys, Inc., Providence, RI (US)

(*) Notice: Subject to any disclaimer, the term of this patent is extended or adjusted under 35 U.S.C. 154(b) by 284 days.

(21) Appl. No.: 13/292,415

(22) Filed: Nov. 9, 2011

(65) Prior Publication Data

US 2012/0122712 A1    May 17, 2012

Related U.S. Application Data

(60) Provisional application No. 61/414,282, filed on Nov. 16, 2010.

(51) Int. Cl.
  *C12Q 1/68*    (2006.01)
  *C07H 21/00*    (2006.01)

(52) U.S. Cl.
  CPC .................... *C12Q 1/6874* (2013.01)
  USPC .......................... 435/6.1; 536/22.1

(58) Field of Classification Search
  CPC ...... C12Q 1/68; C12Q 1/6813; C12Q 1/6816; C12Q 1/6869; C12Q 1/6876
  USPC .......................... 435/6.1; 536/22.1
  See application file for complete search history.

(56) References Cited

U.S. PATENT DOCUMENTS

| | | | |
|---|---|---|---|
| 3,699,437 A | 10/1972 | Ur | |
| H201 H | 1/1987 | Yager | |
| 4,810,650 A | 3/1989 | Kell et al. | |
| 4,874,499 A | 10/1989 | Smith et al. | |
| 5,194,133 A | 3/1993 | Clark et al. | |
| 5,202,231 A | 4/1993 | Drmanac et al. | |
| 5,246,552 A | 9/1993 | Kamiya et al. | |
| 5,314,829 A | 5/1994 | Coles | |
| 5,405,519 A | 4/1995 | Schwartz | |
| 5,427,663 A | 6/1995 | Austin et al. | |
| 5,455,166 A | 10/1995 | Walker | |
| 5,539,082 A | 7/1996 | Nielsen et al. | |
| 5,560,811 A | 10/1996 | Briggs et al. | |
| 5,599,664 A | 2/1997 | Schwartz | |
| 5,650,305 A | 7/1997 | Hui et al. | |
| 5,681,947 A | 10/1997 | Bergstrom et al. | |
| 5,683,881 A | 11/1997 | Skiena | |
| 5,720,928 A | 2/1998 | Schwartz | |
| 5,744,366 A | 4/1998 | Kricka et al. | |
| 5,773,571 A | 6/1998 | Nielsen et al. | |
| 5,795,782 A | 8/1998 | Church et al. | |
| 5,824,477 A | 10/1998 | Stanley | |
| 5,837,115 A | 11/1998 | Austin et al. | |
| 5,908,745 A | 6/1999 | Mirzabekov et al. | |
| 5,972,619 A | 10/1999 | Drmanac et al. | |
| 6,015,714 A | 1/2000 | Baldarelli et al. | |
| 6,020,599 A | 2/2000 | Yeo | |
| 6,025,891 A | 2/2000 | Kim | |
| 6,084,648 A | 7/2000 | Yeo | |
| 6,100,949 A | 8/2000 | Kim | |
| 6,108,666 A | 8/2000 | Floratos et al. | |
| 6,128,051 A | 10/2000 | Kim et al. | |
| 6,147,198 A | 11/2000 | Schwartz | |
| 6,150,089 A | 11/2000 | Schwartz | |
| 6,174,671 B1 | 1/2001 | Anantharaman et al. | |
| 6,182,733 B1 | 2/2001 | McReynolds | |
| 6,210,891 B1 | 4/2001 | Nyren et al. | |
| 6,210,896 B1 | 4/2001 | Chan | |
| 6,258,568 B1 | 7/2001 | Nyren | |
| 6,263,286 B1 | 7/2001 | Gilmanshin et al. | |
| 6,267,872 B1 | 7/2001 | Akeson et al. | |
| 6,274,320 B1 | 8/2001 | Rothberg et al. | |
| 6,294,136 B1 | 9/2001 | Schwartz | |
| 6,303,288 B1 | 10/2001 | Furcht et al. | |
| 6,304,318 B1 | 10/2001 | Matsumoto | |
| 6,340,567 B1 | 1/2002 | Schwartz et al. | |
| 6,355,420 B1 | 3/2002 | Chan | |
| 6,362,002 B1 | 3/2002 | Denison et al. | |
| 6,392,719 B2 | 5/2002 | Kim | |
| 6,400,425 B1 | 6/2002 | Kim et al. | |
| 6,403,311 B1 | 6/2002 | Chan | |
| 6,410,243 B1 | 6/2002 | Wyrick et al. | |
| 6,413,792 B1 | 7/2002 | Sauer et al. | |
| 6,428,959 B1 | 8/2002 | Deamer | |
| 6,448,012 B1 | 9/2002 | Schwartz | |

(Continued)

FOREIGN PATENT DOCUMENTS

| | | | |
|---|---|---|---|
| DE | 19936302 A1 | 2/2001 | |
| EP | 0958495 A1 | 11/1999 | |
| EP | 1486775 A1 | 12/2004 | |
| EP | 1685407 A1 | 8/2006 | |
| JP | 2002526759 A | 8/2002 | |

(Continued)

OTHER PUBLICATIONS

Broude et al. Enhanced DNA sequencing by hybridization. PNAS 91:3072(1994).*
Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).
Alberts, B., et al., (1970) "T4 Bacteriophage Gene 32: A Structural Protein in the Replication and Recombination of DNA," Nature 227:1313-1318.

(Continued)

*Primary Examiner* — Ethan Whisenant
(74) *Attorney, Agent, or Firm* — Goodwin Procter LLP

(57) ABSTRACT

A sequencing method is presented in which a biomolecule is hybridized with a specially chosen pool of different probes of known sequence which can be electrically distinguished. The different probe types are tagged such that they can be distinguished from each other in a Hybridization Assisted Nanopore Sequencing (HANS) detection system, and their relative positions on the biomolecule can be determined as the biomolecule passes through a pore or channel. The methods eliminate, resolve, or greatly reduce ambiguities encountered in previous sequencing methods.

6 Claims, 13 Drawing Sheets

(56) References Cited

U.S. PATENT DOCUMENTS

| | | |
|---|---|---|
| 6,464,842 B1 | 10/2002 | Golovchenko et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,706,203 B2 | 3/2004 | Barth et al. |
| 6,713,263 B2 | 3/2004 | Schwartz |
| 6,723,513 B2 | 4/2004 | Lexow |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,887,714 B2 | 5/2005 | Fritsch et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 6,952,651 B2 | 10/2005 | Su |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,259,342 B2 | 8/2007 | Lin et al. |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,468,271 B2 | 12/2008 | Golovchenko et al. |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,625,706 B2 | 12/2009 | Akeson et al. |
| 7,670,770 B2 | 3/2010 | Chou et al. |
| 7,678,562 B2 | 3/2010 | Ling |
| 7,731,826 B2 | 6/2010 | Hibbs et al. |
| 7,744,816 B2 | 6/2010 | Su et al. |
| 7,824,859 B2 | 11/2010 | Sorge |
| 7,854,435 B2 | 12/2010 | Campbell |
| 7,867,782 B2 | 1/2011 | Barth |
| 7,897,344 B2 | 3/2011 | Dahl et al. |
| 7,939,259 B2 | 5/2011 | Kokoris et al. |
| 8,003,319 B2 | 8/2011 | Polonsky et al. |
| 8,133,719 B2 | 3/2012 | Drmanac et al. |
| 8,232,055 B2 | 7/2012 | Bruhn et al. |
| 8,246,799 B2 | 8/2012 | Oliver et al. |
| 8,262,879 B2 | 9/2012 | Oliver |
| 8,278,047 B2 * | 10/2012 | Oliver et al. ............... 435/6.11 |
| 8,278,050 B2 | 10/2012 | Bailey et al. |
| 8,455,260 B2 * | 6/2013 | Goldstein et al. ............... 436/94 |
| 8,592,182 B2 | 11/2013 | Kokoris et al. |
| 8,628,919 B2 | 1/2014 | Xiao et al. |
| 2002/0127855 A1 | 9/2002 | Sauer et al. |
| 2002/0150961 A1 * | 10/2002 | Bogyo et al. ............... 435/23 |
| 2003/0003609 A1 | 1/2003 | Sauer et al. |
| 2003/0064095 A1 | 4/2003 | Martin et al. |
| 2003/0104428 A1 | 6/2003 | Branton et al. |
| 2003/0143614 A1 | 7/2003 | Drmanac |
| 2003/0186256 A1 | 10/2003 | Fischer |
| 2004/0137734 A1 | 7/2004 | Chou et al. |
| 2004/0146430 A1 | 7/2004 | Dugas |
| 2005/0019784 A1 | 1/2005 | Su et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0084163 A1 | 4/2007 | Lai |
| 2007/0178240 A1 | 8/2007 | Yamazaki et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |
| 2008/0085840 A1 | 4/2008 | Buzby |
| 2008/0119366 A1 | 5/2008 | Sauer et al. |
| 2008/0242556 A1 | 10/2008 | Cao et al. |
| 2008/0254995 A1 | 10/2008 | Kim et al. |
| 2009/0005252 A1 | 1/2009 | Drmanac et al. |
| 2009/0011943 A1 | 1/2009 | Drmanac et al. |
| 2009/0099786 A1 | 4/2009 | Oliver et al. |
| 2009/0111115 A1 | 4/2009 | Drmanac et al. |
| 2009/0136948 A1 | 5/2009 | Han et al. |
| 2009/0143234 A1 * | 6/2009 | Palaniappan ............... 506/4 |
| 2009/0214392 A1 | 8/2009 | Kameoka et al. |
| 2010/0078325 A1 | 4/2010 | Oliver |
| 2010/0096268 A1 | 4/2010 | Ling et al. |
| 2010/0143960 A1 | 6/2010 | Bazin |
| 2010/0243449 A1 | 9/2010 | Oliver |
| 2012/0074925 A1 | 3/2012 | Oliver |
| 2012/0208193 A1 | 8/2012 | Okino et al. |
| 2013/0011934 A1 * | 1/2013 | Oliver et al. ............... 436/501 |
| 2014/0087390 A1 | 3/2014 | Oliver et al. |

FOREIGN PATENT DOCUMENTS

| | | |
|---|---|---|
| JP | 2003-028826 A | 1/2003 |
| JP | 2003510034 A | 3/2003 |
| JP | 2003513279 A | 4/2003 |
| JP | 2004004064 A | 1/2004 |
| JP | 2007068413 A | 3/2007 |
| WO | WO-9004652 | 5/1990 |
| WO | WO-9322678 A2 | 11/1993 |
| WO | WO-9617957 | 6/1996 |
| WO | WO-2008069973 | 11/1997 |
| WO | WO-9835012 A2 | 8/1998 |
| WO | WO-0009757 | 2/2000 |
| WO | WO-0020626 A1 | 4/2000 |
| WO | WO-0022171 | 4/2000 |
| WO | WO-0062931 A1 | 10/2000 |
| WO | WO-0118246 A1 | 3/2001 |
| WO | WO-0131063 A1 | 5/2001 |
| WO | WO-0133216 A1 | 5/2001 |
| WO | WO-0137958 | 5/2001 |
| WO | WO-0142782 | 6/2001 |
| WO | WO-0146467 A2 | 6/2001 |
| WO | WO-0207199 | 1/2002 |
| WO | WO-0250534 | 6/2002 |
| WO | WO-03000920 A2 | 1/2003 |
| WO | WO-03010289 | 2/2003 |
| WO | WO-03079416 | 9/2003 |
| WO | WO-03089666 A2 | 10/2003 |
| WO | WO-03106693 | 12/2003 |
| WO | WO-2004035211 A1 | 4/2004 |
| WO | WO-2004085609 A2 | 10/2004 |

(56) References Cited

FOREIGN PATENT DOCUMENTS

| WO | WO-2005017025 |   | 2/2005 |
|----|---------------|---|--------|
| WO | WO-2006020775 |   | 2/2006 |
| WO | WO-2006028508 |   | 3/2006 |
| WO | WO-2006052882 |   | 5/2006 |
| WO | WO-2007/041621 A2 |   | 4/2007 |
| WO | WO-2007106509 |   | 9/2007 |
| WO | WO-2007111924 |   | 10/2007 |
| WO | WO-2007127327 |   | 11/2007 |
| WO | WO-2008021488 |   | 2/2008 |
| WO | WO-2008039579 |   | 4/2008 |
| WO | WO-2008042018 |   | 4/2008 |
| WO | WO-2008046923 |   | 4/2008 |
| WO | WO-2008049021 |   | 4/2008 |
| WO | WO-2008079169 |   | 7/2008 |
| WO | WO 2009/046094 | * | 4/2009 |
| WO | WO-2010002883 A2 |   | 1/2010 |
| WO | WO-2010111605 A2 |   | 9/2010 |
| WO | WO-2010138136 A1 |   | 12/2010 |
| WO | WO-2011109825 A2 |   | 9/2011 |
| WO | WO-2014052433 A2 |   | 4/2014 |

OTHER PUBLICATIONS

Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.

Arratia, R., et al., (1989) "Poisson Process Approximation for Repeats in One Sequence and Its Application to Sequencing by Hybridization," Dept. of Mathematics, University of Southern California.

Ashkin, "Optical trapping and manipulation of neutral particles using lasers," Proc. Natl. Acad. Sci. USA, vol. 94, DD. 4853-4860, May 1997.

Austin, M., et al., (2004) "Fabrication of 5 nm Linewidth and 14 nm Pitch Features by Nanoimprint Lithography," App. Phys. Lett. 84:5299-5301.

Bains, W., et al., (1988) "A Novel Method for Nucleic Acid Sequence Determination," J. Theor. Biol. 135:303-307.

Baliga, R., et al., (2001) "Kinetic Consequences of Covalent Linkage of DNA Binding Polyamides," Biochemistry 40:3-8.

Ben-Dor et al, "On the Complexity of Positional Sequencing by Hybridization", Journal of Computational Biology, vol. 8, No. 4, 2001, pp. 361-371.

Bennett et al. Pharmacogenomics (2005) 6:373-382.

Bianco, P., et al., "Interaction of the RecA Protein of *Escherichia coli* with Single-Stranded Oligodeoxyribonucleotides," Nucleic Acids Research vol. 24. No. 24 (1996) 4933-4939.

Bloom, et al, Applications of Numbered Undirected Graphs, Proceedings of the IEEE, vol. 65, No. 4, Apr. 1977, pp. 562-570.

Branton, Daniel et al, "The potential and challenges of anopore sequencing," Nature Biotechnology, vol. 26, No. 10, Oct. 2008, pp. 1146-1153.

Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.

Buchmueller, K.L., et. al., (2006) "Physical and Structural Basis for the Strong Interactions of the -ImPy- Central Pairing Motif in the Polyamide f-ImPylm," Biochemistry 45:13551-13565.

Cao, H., et al., (2002) "Fabrication of 10 nm Enclosed Nanofluidic Channels," Applied Physics Letters 81(1): 174-176.

Cao, H., et al., (2002) "Gradient Nanostructures for Interfacing Microfluidics and Nanofluidics," Applied Physics Letters 81:3058-3060.

Chen, C., et al., (1994) "Analogous Organic Synthesis of Small-Compound Libraries: Validation of Combinatorial Chemistry in Small-Molecule Synthesis," J. Am. Chem. Soc. 116:2661-2662.

Chen, P., et al., (2004) "Probing Single DNA Molecule Transport Using Fabricated Nanopores," Nano Letters 4:2293-2298.

Chetverin, A., et al., (1994) "Oligonucleotide Arrays: New Concepts and Possibilities," Bio/Technology 12:1093-1099.

Cox, M. (2007) "Motoring Along with the Bacterial RecA Protein," Nature Reviews—Molecular Cell Biology 9:127-138.

Dervan, P.B. (2001) "Molecular Recognition of DNA by Small Molecules," Bioorg. Med. Chem. 9:2215-2235.

Dervan, P.B., et al., (2003) "Recognition of the DNA minor groove by pyrrole-imidazole polyamides," Curr. Op. Struc. Biol. 13:284-299.

Doss, R.M., et al., (2006) "Programmable Oligomers for Minor Groove DNA Recognition," J. Am. Chem. Soc. 128:9074-9079.

Drmanac, R., et al. (1989) "Sequencing of Megabase Plus DNA by Hybridization: Theory of the Method," Genomics 4:114-128.

Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.

Farkas, Z., et al., (2003) "DNA Uptake Into Nuclei: Numerical and Analytical Results," J. Phys.: Condens. Matter 15:S1767-S1777.

Fechter, E.J., et al., (2005) "Sequence-specific Fluorescence Detection of DNA by PolyamideThiazole Orange Conjugates," J. Am. Chem. Soc. 127:16685-16691.

Floreancig, P.E., et al., (2000) "Recognition of the Minor Groove of DNA by Hairpin Polyamides Containing □ -Substituted-, □ -Amino Acids," J. Am. Chem. Soc. 122:6342-6350.

Fodor, S., et al., (2005) "Light-Directed, Spatially Addressable Parall Chemical Synthesis" Research Article 6 pgs.

Fologea, D., et al., (2005) "Slowing DNA Translocation in a Solid-State Nanopore," Nano Lett. 5(9):1734-7.

Frieze, A., et al., (1999) "Optimal Reconstruction of a Sequence From its Probes," 12 pgs.

Gerland, U., et al., (2004) "Translocation of Structured Polynucleotides Through Nanopores," Phys. Biol. 1:19-26.

Gershow, M., et al., (2007) "Recapturing and Trapping Single Molecules with a Solid-State Nanopore," Nature Nanotech. 2:775-779.

Ghosh, et al, Detection of Double-Stranded DNA: molecular methods and applications for DNA diagnostics Molecular Biosystems (2006) vol. 2, pp. 551-560.

Giehart B., et al., (2008) "Nanopore with transverse nanoelectrodes for electrical characterization and sequencing of DNA" Sensors and Actuators B., Elsevier Sequoia S.A, ScienceDirect,132:2.

Gracheva, M., et al., (2002) "Simulation of the Electric Response of DNA Translocation through a Semiconductor Nanopore-Capacitor," Nanotechnology 17:622-633.

Guo, L. (2004) "Recent Progress in Nanoimprint Technology and its Application," J. Phys. D: Appl. Phys 37:R123-R141 (Appendices B-D).

Gygi, M.P., et al., (2002) "Use of fluorescent sequence-specific polyamides to discriminate human chromosomes by microscopy and flow cytometry," Nucleic Acids Research 30:2790-2799.

Halby, L., et al., (2005) "Functionalized head-to-head hairpin polyamides: Synthesis, double-stranded DNA-binding activity and affinity," Bioorg. Med. Chem. Lett. 15:3720-3724.

Heller, C., (2001) "Principles of DNA Separation with Capillary Electrophoresis," Electrophoresis 22:629-643.

Heng, J., et al., (2004) "Sizing DNA Using a Nanometer-Diameter Pore," Biophysical Journal 87:2905-2911.

Hudson, B., (1999) "An Experimental Study of SBH with Gapped Probes," 50 pgs.

International Preliminary Report on Patentability issuance date Apr. 7, 2010, PCT/US2008/078432.

International Preliminary Report on Patentability, Application No. PCT/US2009/055878, mailed Nov. 29, 2011, 9 pages.

International Preliminary Report on Patentability, issuance of report Mar. 8, 2011, Application No. PCT/US2009/055876.

International Search Report and Written Opinion dated Jun. 29, 2010, PCT/US09/055876, 13 pages.

International Search Report and Written Opinion dated Mar. 24, 2010 for PCT/US09/055878, 13 pages.

International Search Report and Written Opinion dated May 2, 2009, PCTUS2008/078432.

International Search Report and Written Opinion dated Sep. 30, 2010, PCT/US2010/028848, 14 pgs.

(56) References Cited

OTHER PUBLICATIONS

International Search Report and Written Opinion for PCT/US09/558876 dated Feb. 10, 2010.
International Search Report and Written Opinion, PCT/US2011/059933, dated Apr. 2, 2012.
International Search Report for PCT/US04/04138, mailed May 4, 2006, 5 pages.
Jonsson, U., et al., (1991) "Real-Time Biospecific Interaction Analysis Using Surface Plasmon Resonance and a Sensor Chip Technology," BioTechniques, 11:620-627.
Ju et al., Proc. Nat. Acad. Sci. USA (2006) 103:19635-19640.
Kalaugher, L., (2002) "Diffraction Gradient Lithography Aids Nanofluidics," Nanotechweb.org.
Kanehisa, L. (1984) "Use of Statistical Criteria for Screening Potential Homologies in Nucleic Acid Sequences," Nucleic Acids Research 12:203-213.
Kasianowicz et al., "Characterization of Individual Polynucleotide Molecules Using a Membrane Channel," Proc. Nat. Acad. Sci. USA 93:13770-13773 (1996).
Khrapko, K.R. et al., (1989) "An Oligonucleotide Hybridizatioin Approach to DNA Sequencing," FEBS Lett. 256:118-22.
Kim, C., et al., (1992) "Binding Properties of Replication Protein A from Human and Yeast Cells," Mol. and Cell. Bio. 12(7):3050-3059.
Kuo, et al., "Hybrid three-dimensional nanofluidic/microfluidic devices using molecular gates," Sensors and Actuators A, vol. 102 (Oct. 2002):223-233.
Langa, "Self-organized growth of single crystals of nanopores," Applied Physics Letters, AIP, American Institute of Physics, 2003, vol. 82, No. 2, pp. 278-280.
Li et al., "Lon-beam sculpting at nanometre length scales", Nature 412,166-169 (2001).
Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.
Liang, X., et al., (2008) "Nanogap Detector Inside Nanofluidic Channel for Fast Real Time Label-Free DNA Analysis," Nano Letters 8:1472-76.
Ling, X., et al., "Hybridization Assisted Nanopore Sequencing," Patent Specification, 32 pgs.
Loakes, D., et al., (1994) "5-Nitroindole as an Universal Base Analogue," Nucleic Acids Research 22:4039-4043.
Loakes, D., et al., (1995) "3-Nitropyrrole and 5-Nitroindole as Universal Bases in Primers for DNA Sequencing and PCR," 23:2361-2366.
Lohman, T., et al., (1994) "*Escherichia Coli* Single-Stranded DNA-Binding Protein: Multiple DNA-Binding Modes and Cooperatives," Annu. Rev. Biochem. 63:527-70.
Losi, et al., "Time-Resolved Absorption and Photothermal Measurements with Recombinant Sensory Rhodopsin II from *Natronobacterium pharaonis*," Biophys. J. 77, 3277-3286, Dec. 1999.
Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].
Margulies et al., (2005) Nature 437:376-380.
Marques, M.A., et al., (2004) "Expanding the Repertoire of Heterocycle Ring Pairs for Programmable Minor Groove DNA Recognition," J. Am. Chem. Soc. 126:10339-10349.
McEntee, K., et al. "Binding of the RecA Protein of *Escherichia Coli* to Single- and Double-Stranded DNA." J. Biol. Chem. (1981) 256:8835.
Meller, A., et al., (2000) "Rapid Nanopore Discrimination Between Single Polynucleotide Molecules," PNAS 97:1079-1084.
Meller, et al., "Voltage-driven DNA translocations through a nanopore," Phys. Rev. Lett. 86(15),3435-3438 (2001).
Nice, E., et al., (1993) "Mapping of the Antibody- and Receptor-Binding Domains of Granulocyte Colony-Stimulating Factor Using an Optical Biosensor," Journal of Chromatography 646:159-168.

Nichols, R., et al., (1994) "A Universal Nucleoside for Use at Ambiguous Sites in DNA Primers," Letters to Nature 369:492-493.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.
Optical Tweezers: Introduction to Optical Tweezers, Retrieved Apr. 21, 2010 from http://www.nbi.dk/~tweezer/introduction.htm, pp. 1.5.
Pablo, P.J., et al., (2000) "Absence of dc-Conductivity." Phys. Rev. Lett. 85:4992-4995.
Partial International Search Report dated Feb. 15, 2010 for PCT/US09/055878, 3 pages.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P. et al., (1991) "Improved Chips for Sequencing by Hybridization," Journal of Biomolecular Structure & Dynamics 9:399-410.
Pevzner, P., (1989) "1-Tuple DNA Sequencing: Computer Analysis," Journal of Biomolecular Structure & Dynamics 7:63-73.
Powell, M., et al., (1993) "Characetrization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et. al., (2000) "Sequencing-by-Hybridization at the Information-Theory Bound: An Optimal Algorithm," J. Comp. Biol. 7: 621-630.
Quake et al. Proc. Nat. Acad. Sci. USA (2003) 100:3960-3964.
Riehn, R. et al., (2005) Proc. Nat. Acad. Sci., 102:1012.
Robertson, J., et al., (2007) "Single-Molecule Mass Spectrometry in Solution Using a Solitary Nanopore," PNAS 104:8207-8211.
Rucker, V.C., et al., (2003) "Sequence Specific Fluorescence Detection of Double Strand DNA," J. Am. Chem. Soc. 125:1195-1202.
Sanger, F. et al., (1977) "DNA Sequencing with Chain-Terminating Inhibitors," Proc. Natl. Acad. Sci. USA 12:5463-5467.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Storm, A., et al., (2005) "Fast DNA Translocation through a Solid-State Nanopore," Nano Letters 5(7):1193-1197.
Storm, et al., "Fabrication of solid-state nanopores with single-nanometre precision," Nature Materials 2,537-540, Auaust 2003.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, "Less is more," Nature 412, 135-136, Jul. 2001.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Written Opinion dated Jul. 1, 2008, PCT/US06/38748.

(56) References Cited

OTHER PUBLICATIONS

Zhang, W., et al., (2006) "Discrimination of Hairpin Polyamides with an □ Substituted-□ -aminobutyric Acid as a 5'-TG-3' Reader in DNA Minor Groove," J. Am. Chem. Soc. 128:8766-8776.
Zwolak, M., et al., (2008) "Physical Approaches to DNA Sequencing and Detection." Rev. Mod. Phy. 80:141-165 (J).
Anderson, P. et al., "Nkx3.1 and Myc crossregulate shared target genes in mouse and human prostate tumorigenesis," J. Clinical Investigation, May 2012, pp. 1907-1919, vol. 122, http://www.jci.org.
Arrowsmith, C. et al., "Epigenetic protein families: a new frontier for drug discovery," Nature Reviews: Drug Discovery, May 2012, pp. 384-400, vol. 11, Macmillan Publishers Limited.
Austin, Robert, "The art of sucking spaghetti", Nature Publishing Group, Nature Materials, vol. 2, pp. 567-568, Sep. 2003.
Bourdoncle, A., et al., "Quaruplex-Based Molecular Beacons as Tunable DNA Probes", J. Am. Chem. Soc., vol. 128, No. 34, pp. 11094-11105, 2006.
Examination Report mailed Feb. 7, 2013 in European Application No. 10 717 908.7-1240 (4 pages).
Examination Report mailed Mar. 4, 2013 in European Application No. 08 835 216.6-1404 (6 pages).
Greer, E. et al., "Histone methylation: a dynamic mark in health, disease and inheritance," Nature Review: Genetics, May 2012, pp. 343-357, vol. 13, Macmillan Publishers Limited.
Hannenhalli S. et al. Comput Appl Biosci (1996) 12 (1): 19-24.
Heyn, H. et al., "DNA methylation profiling in the clinic: applications and challenges," Nature Review: Genetics, Oct. 2012, pp. 679-692, vol. 13, Macmillan Publishers Limited.
International Preliminary Report on Patentability in PCT/US2012/024708 mailed Aug. 13, 2013.
International Preliminary Report on Patentability, Application No. PCT/US2011/053274, issuance date May 28, 2013, 14 pages.
International Preliminary Report on Patentability, Application No. PCT/US2011/059933, issuance date May 21, 2013, 8 pages.
International Search Report and Written Opinion dated Oct. 25, 2012, PCT/US12/024708.
International Search Report and Written Opinion, PCT/US2011/053274, dated May 2, 2013.
Invitation to Pay Additional Fees and, Where Applicable, Protest Fee & Partial International Search dated Feb. 15, 2013, PCT/US2011/053274, 9 pages.
Invitation to Pay Additional Fees and, Where Applicable, Protest Fee & Partial International Search dated Mar. 3, 2014, PCT/US2012/061651, 5 pages.
Koike, Shinji et al., "Investigation into the Degrading Mechanism of Positive Electrodes after Calendar Life Test Using Transmission Electron Microscopy", 214th ECS Meeting, Abstract #569, The Electrochemical Society, Osaka, Japan, 1 page, 2008.
Langer-Safer, P. et al., "Immunological method for mapping genes on Drosophila polytene chromosomes," Proc. Natl. Acad. Sci. USA, Jul. 1982, pp. 4381-4385, vol. 79.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Notice of Reasons for Rejection mailed Jun. 17, 2013 in Japanese Patent Application No. 2011-525300.
Notification of the First Office Action mailed Sep. 28, 2012 in Chinese Patent Application No. 200980140663.0.
Notification of the Second Office Action mailed Apr. 2, 2013 in Chinese Patent Application No. 200980140663.0.
Olasagasti, F.; Lieberman, K. R.; Benner, S.; Cheri, G. M.; Dahl, J. M.; Deamer, D. W.; Akeson, M. *Nat. Nanotechnol.* 2010, 5, 798-806.
Park, P., "ChIP-seq: advantages and challenges of a maturing technology," Nature Reviews: Genetics, Oct. 2009, pp. 669-680, vol. 10, Macmillan Publishers Limited.
Pastor, W. et al., "Genome-wide mapping of 5-hydroxymethylcytosine in embryonic stem cells," Nature, May 19, 2011, pp. 394-397, vol. 473, Macmillan Publishers Limited.
Rapley, Ralph, "Direct Sequencing of PCR Products with DNA-Binding Proteins", Methods in Molecular Biology, vol. 65, Humana Press Inc., Totowa, NJ, pp. 101-104, 1996.
Rapley, Ralph, "Enhancing PCR Amplification and Sequencing Using DNA-Binding Proteins", Molecular Biotechnology, vol. 2, pp. 295-298, 1994.
Rehrauer, William M. et al., "Alteration of the Nucleoisude Triphosphate (NTP) Catalytic Domain within *Escherichia coli* recA Protein Attenuates NTP Hydrolysis but Not Joint Molecule Formation*", pp. 1292-1297, The Journal of Biological Chemistry, The American Society for Biochemistry and Molecule Biology, Inc., vol. 268, No. 2, Jan. 15, 1993.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Ross-Innes, C. et al., "Differential oestrogen receptor binding is associated with clinical outcome in breast cancer," Nature, Jan. 2012, pp. 389-394, vol. 481, Macmillan Publishers Limited.
Shim et al., "Detection and Quantification of Methylation in DNA using Solid-State Nanopores", Scientific Reports, www.nature.com, Mar. 11, 2013, pp. 1-8.
Shoaib, M. et al., "Pub-NChIP-"in vivo biotinylation" approach to study chromatin in proximity to a protein of interest," Genome Research, 2013, pp. 331-340, vol. 23, Cold Spring Harbor Laboratory Press, www.genome.org.
van Steensel, B. et al., "Identification of in vivo DNA targets of chromatin proteins using tethered Dam methyltransfarase," Nature Biotechnology, Apr. 2000, pp. 424-428, vol. 18.
Venkatesan et al., "Stacked Graphene-Al2O3 Nanopore Sensors for Sensitive Detection of DNA and DNA-Protein Complexes", www.acsnano.org, vol. 6, No. 1, 2012, pp. 441-450.
Waugh, David S., "Make the most of affinity tags", pp. 316-320, Trends in Biotechnology, Science Direct, vol. 23, No. 6, Jun. 2005.
Web article (2003) "DNA Combed Into Nanochannels," http://www.nature.com.
Written Opinion dated Jul. 1, 2008, PCT/US06/38748, 6 pages.
Zhang, W., et al., (2006) "Discrimination of Hairpin Polyamides with an α-Substituted-γaminobutyric Acid as a 5'-TG-3' Reader in DNA Minor Groove," J. Am. Chem. Soc. 128:8766-8776.
Zwolak, M., et al., (2008) "Colloquium: Physical Approaches to DNA Sequencing and Detection." Rev. Mod. Phy. 80:141-165 (J).

* cited by examiner

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
agacctgcta                                                          10

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gctagcagta gcatagcacc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gctagcatag cagtagcacc                                               20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 4
aactgcggaa atctgagcat tac                                          23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cccatgatga gtgatgtatt                                              20
```

METHODS FOR SEQUENCING A BIOMOLECULE BY DETECTING RELATIVE POSITIONS OF HYBRIDIZED PROBES

CROSS-REFERENCE TO RELATED APPLICATIONS

This application claims priority to and the benefit of, and incorporates herein by reference in its entirety, U.S. Provisional Patent Application No. 61/414,282, which was filed on Nov. 16, 2010.

SEQUENCE LISTING

The instant application contains a Sequence Listing which has been submitted in ASCII format via EFS-Web and is hereby incorporated by reference in its entirety. Said ASCII copy, created on Dec. 21, 2011, is named NAB-010.txt and is 1,443, bytes in size.

FIELD OF THE INVENTION

This invention relates generally to methods for sequencing a biomolecule. More particularly, in certain embodiments, the invention relates to determining the sequence of a biomolecule from the relative positions of hybridized probes.

BACKGROUND OF THE INVENTION

Biopolymer sequencing refers to the determination of the order of nucleotide bases—adenine, guanine, cytosine, and thymine—in a biomolecule, e.g., a DNA or RNA molecule, or portion thereof. Biomolecule sequencing has numerous applications, for example, in diagnostics, biotechnology, forensic biology, and drug development. Various techniques have been developed for biopolymer sequencing.

Sequencing by Hybridization (SBH) is a method for biomolecule sequencing in which a set of single stranded fragments or probes (generally, all possible $4^k$, oligonucleotides of length k) are attached to a substrate or hybridization array. The array is exposed to a solution of single-stranded fragments of DNA. Hybridization between the probes and the DNA reveals the spectrum of the DNA, i.e., the set of all k-mers that occur at least once in the sequence. Determining a sequence using SBH involves finding an Eulerian path (a path that traverses all edges) of a graph representing the spectrum of detected k-mers. Convergence on a single solution occurs when only one sequence for the k-mers is consistent with the spectrum. Ambiguous sequencing occurs when more than one sequence for the hybridized k-mers is consistent with the spectrum. Current SBH techniques are limited because any sufficiently dense graph with one solution has multiple, equally well-supported solutions.

Hybridization Assisted Nanopore Sequencing (HANS) is a method for sequencing genomic lengths of DNA and other biomolecules, involving the use of one or more nanopores, or alternatively, nanochannels, micropores, or microchannels. HANS involves hybridizing long fragments of the unknown target with short probes of known sequence. The method relies on detecting the position of hybridization of the probes on specific portions of the biomolecule (e.g., DNA) to be sequenced or characterized. The probes bind to the target DNA wherever they find their complementary sequence. The distance between these binding events is determined by translocating the target fragments through a nanopore (or nanochannel, micropore, or microchannel). By reading the current or voltage across the nanopore, it is possible to distinguish the unlabeled backbone of the target DNA from the points on the backbone that are binding sites for probes. Since DNA translocates at an approximately constant velocity, a time course of such current or voltage measurements provides a measurement of the relative distance between probe binding sites on the target DNA.

After performing these measurements for each kind of probe, one at a time, the DNA sequence is determined by analyzing the probe position data and matching up overlapping portions of probes. However, due to inaccuracies associated with measuring absolute probe positions using HANS, sequencing ambiguities may still arise.

There is a need for improved methods for sequencing biomolecules that are able to avoid or resolve the ambiguities encountered with current SBH, HANS, and other sequencing techniques.

SUMMARY OF THE INVENTION

A sequencing method is presented in which a biomolecule is hybridized with not just one type of probe, but with a specially chosen pool of different probes of known sequence which can be electrically distinguished. The different probe types are tagged such that they can be distinguished from each other in a Hybridization Assisted Nanopore Sequencing (HANS) detection system, and their relative positions on the biomolecule can be determined as the biomolecule passes through a pore or channel. In certain embodiments, by allowing relative probe positions to be directly determined, the methods eliminate or greatly reduce ambiguities encountered in previous sequencing methods.

It is difficult, if not impossible, to use an unlimited number of tags to distinguish many different probes hybridized at once onto a single biomolecule, because the accuracy and ability to distinguish electrical signals in the HANS approach is limited. Thus, methods presented herein use a series of pools of probes of known sequence, each having several (e.g., four) members, which are hybridized to the biomolecule one pool at a time (or one partial pool at a time). The relative positions of the four probes from a given pool on the biomolecule are determined via HANS. As explained herein, it is possible to use four, three, or even as few as two distinguishable tags in a given passage of the hybridized biomolecule through the pore or channel in order to achieve the benefits of this method. Thus, the sequencing methods work within the sensitivity limitations of current HANS systems.

As used herein, the term "sequence" is not limited to an entire sequence but may include subsequences of a biomolecule, and the term "biomolecule" is not limited to an entire biomolecule but may include fragments of a biomolecule. The term "biomolecule" may include one or more copies of a given biomolecule (or fragment thereof). For example, where a biomolecule is hybridized with one or more probes, this may mean hybridizing a large number of copies of a given biomolecule with many copies of the one or more probes.

In one aspect, the invention relates to a method of determining a sequence of a biomolecule. The method, which may be referred to as distinguishable tagging sequencing by hybridization (dtSBH), includes the steps of: (a) identifying a set of k-1-length subsequences that represent a plurality of substrings of a sequence string s of the biomolecule; (b) for each of the k-1-length subsequences, identifying a pool of four different k-mer extensions of the k-1-length subsequence; (c) for each pool identified in step (b): (i) hybridizing the biomolecule with the four k-mer probes making up the pool; and (ii) detecting relative positions of the k-mer probes that have attached to the biomolecule; and (d) ordering the subsequences corresponding to the detected attached probes to determine the sequence string s of the biomolecule. In certain embodiments, steps (c)(i) and (c)(ii) can be performed in multiple steps and with fewer than all four k-mer probes hybridized to the biomolecule at a time.

In certain embodiments, each of the four k-mer probes in step (c) has a distinguishable tag attached, such that there are four different detectable tags used for a given pool of k-mers. In certain embodiments, step (c)(i) includes hybridizing the biomolecule with all four of the k-mer probes making up the pool prior to detecting the relative positions of the attached k-mer probes in step (c)(ii), such that step (c)(ii) results in detecting the relative positions of all four of the k-mer probes making up the pool.

In certain embodiments, as few as two distinguishable tags can be used at a time. For example, in certain embodiments, step (c) comprises: (A) hybridizing the biomolecule with two different k-mer probes selected from the four k-mer probes making up the pool, wherein the two selected k-mer probes have tags attached that are distinguishable from each other (e.g., there are two different species/kinds of tags used, and the biomolecule is hybridized with copies of the two different k-mer tags); (B) following (A), where one or more binding events occur involving both of the selected k-mer probes, detecting relative positions of the two different k-mer probes that have attached to the biomolecule; and (C) repeating (A) and (B) with another two different k-mer probes (e.g., these are two species/kinds of k-mer probes, different from each other) selected from the four k-mer probes making up the pool until hybridizations and detections are performed for all six pair combinations of the four k-mer probes making up the pool, thereby detecting the relative positions of all four of the k-mer probes making up the pool.

In certain embodiments, three distinguishable tags can be used at a time. For example, in certain embodiments, step (c) includes: (A) hybridizing the biomolecule with a set of three k-mer probes selected from the four k-mer probes making up the pool, wherein the three selected k-mer probes have tags attached that are distinguishable from each other (e.g., these are three different species/kinds of tags, and the biomolecule is hybridized with many copies of the three different k-mer probes); (B) following (A), where one or more binding events occur involving two or three of the selected k-mer probes, detecting relative positions of the two or three k-mer probes that have attached to the biomolecule; and (C) repeating (A) and (B) with a different set of three k-mer probes (e.g., these are three species/kinds of k-mer probes, different from each other) selected from the four k-mer probes making up the pool until hybridizations and detections are performed for all four three-member combinations of the four k-mer probes making up the pool, thereby detecting the relative positions of all four of the k-mer probes making up the pool. In certain embodiments, other combinations of the four k-mer probes with multiple, distinguishable tags are possible.

In certain embodiments, step (c)(ii) includes using HANS to detect the relative positions of the k-mer probes. HANS is Hybridization Assisted Nanopore Sequencing wherein the distance between binding events may be measured, for example, by sending a target biomolecule and the probes attached (hybridized) thereto through a nanopore, nanochannel, micropore, or microchannel. In certain embodiments, step (c)(ii) includes monitoring an electrical signal across a fluidic channel or pore or within a fluidic volume of a channel or pore as the hybridized biomolecule translocates therethrough, the electrical signal being indicative of hybridized portions of the biomolecule and non-hybridized portions of the biomolecule. In certain embodiments, the detected electrical signal allows differentiation between at least two of the k-mer probes hybridized to the biomolecule. In certain embodiments, step (c)(ii) includes detecting an optical signal indicative of the relative position of at least two of the k-mer probes hybridized to the biomolecule.

In certain embodiments, the set of k-1-length subsequences represents all possible substrings of length k-1, in the sequence string s. In certain embodiments, k is an integer from 3 to 10,, for example, 4, 5, 6,, or 7. In certain embodiments, s is a sequence string at least 100, bp in length, for example, a string at least 1000, bp in length, at least 5000, by in length, at least 100,000 bp in length, at least 1, million bp in length, or at least 1, billion bp in length.

In another aspect, the invention relates to a HANS algorithm with positional averaging for resolution of branching ambiguities. The method may be referred to as moving-window SBH or Nanopore-assisted SBH, with enhanced ambiguity resolution. The method determines a sequence of a biomolecule and includes the steps of: (a) identifying a spectrum of k-mer probes that represent a plurality of substrings of a sequence string s of the biomolecule; (b) arranging the substrings to form a plurality of candidate superstrings each containing all the substrings in step (a), wherein each candidate superstring has a length corresponding to the shortest possible arrangement of all the substrings; (c) identifying an ambiguity in the ordering of two or more branches common to the candidate superstrings and identifying a plurality of k-mer probes corresponding to the substrings along each of the two or more branches; (d) for each k-mer probe identified in step (c), hybridizing the biomolecule with the k-mer probe and obtaining an approximate measure of absolute position of the k-mer probe along the biomolecule; (e) determining a relative order of the two or more branches by, for each branch, obtaining an average of the measures of absolute position of each k-mer probe identified in step (c) that are in the branch, and ordering the two or more branches according to the average absolute position measures identified for each branch, thereby identifying the sequence string s of the biomolecule.

In certain embodiments, identification of the spectrum of k-mer probes in step (a) is performed at the same time the approximate measure of absolute position is obtained in step (d) (e.g., where both step (a) and (d) can be performed by HANS). In certain embodiments, step (a) is performed by SBH with step (d) being performed by HANS.

In certain embodiments, steps (a) and (d) are performed simultaneously. In certain embodiments, steps (a) and (d) are performed using HANS. In certain embodiments, step (a) is performed using SBH.

In certain embodiments, step (d) includes monitoring an electrical signal across a fluidic channel or pore or within a fluidic volume of a channel or pore as the hybridized biomolecule translocates therethrough, the electrical signal being indicative of hybridized portions of the biomolecule and non-hybridized portions of the biomolecule. In certain embodiments, the spectrum of k-mer probes represents a complete set of substrings of the sequence string s.

The description of elements of the embodiments above can be applied to this aspect of the invention as well.

In yet another aspect, the invention relates to an apparatus for determining a sequence of a biomolecule, the apparatus comprising: (a) memory that stores code defining a set of instructions; and (b) a processor that executes said instructions thereby to order subsequences corresponding to detected probes attached to the biomolecule to determine a sequence string s of the biomolecule using data obtained by, for each pool of four different k-mer extensions of k-1-length subsequences of sequence string s, hybridizing the biomolecule with the four k-mer probes making up the pool, and detecting relative positions of the k-mer probes that have attached to the biomolecule.

The description of elements of the embodiments above can be applied to this aspect of the invention as well.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

FIG. 1 discloses SEQ ID NO: 4.

FIG. 5 discloses SEQ ID NO: 1.

FIG. 6 discloses SEQ ID NO: 5.

FIG. 7 discloses SEQ ID NO: 2, and SEQ ID NO: 3, respectively, in order of appearance.

DETAILED DESCRIPTION

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Figure 1:
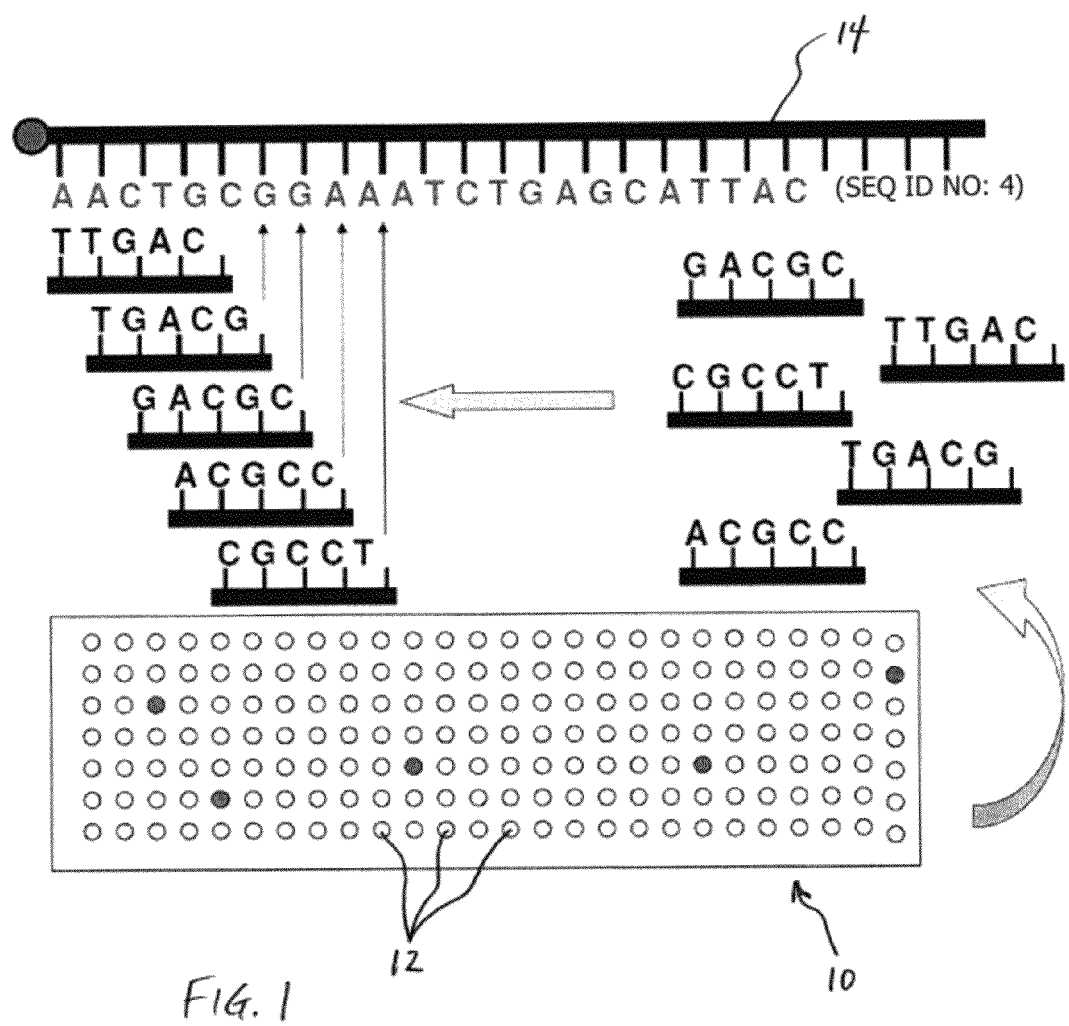
FIG. 1 is a schematic diagram of an SBH hybridization array, according to an illustrative embodiment of the invention.

SBH is a method for recovering the sequence of a biomolecule string s. The spectrum of string s with respect to an integer k is the set of strings of length k (i.e., k-mers) that are substrings of s (i.e., k-mers that occur at least once in the sequence of string s). As depicted in FIG. 1, in traditional SBH, the spectrum of string s is obtained using a hybridization array 10. A k-mer hybridization array 10 has a spot 12 of DNA for each probe of length k, for a total of $4^k$ spots. Target DNA 14 is washed over the array 10 and hybridizes or sticks to each spot 12 that has a complement in the target 14. By identifying the spots 12 where k-mers hybridized to the target 14, the spectrum of the target 14 is revealed.

Figure 2:
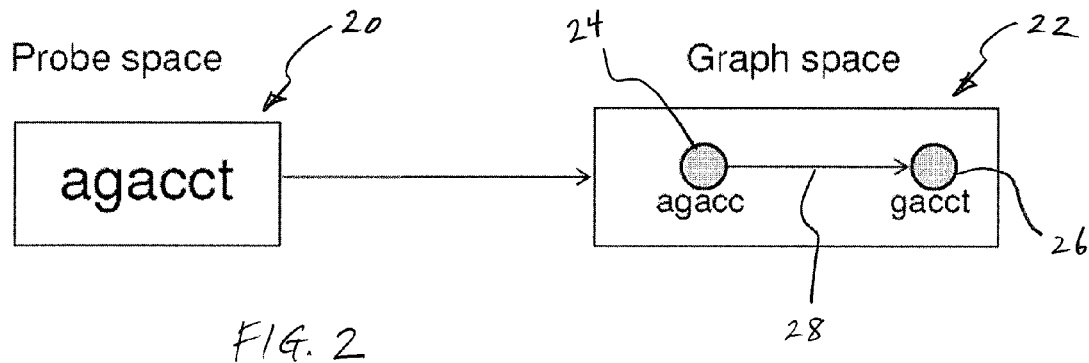
FIG. 2 is a schematic diagram of a spectrum and a graph space of a biomolecule, according to an illustrative embodiment of the invention.

The spectrum or probe space of string s may be represented graphically in a graph space in which each probe is an edge from its k-1-mer prefix to its k-1-mer suffix. For example, referring to FIG. 2, when a spectrum 20 or probe space consists of a single probe "agacct," a graph space 22 includes a first node 24 corresponding to the k-1-mer prefix "agacc," a second node 26 corresponding to the k-1-mer suffix "gacct," and an arrow 28, from the first node 24 to the second node 26, representing the path from the prefix to the suffix.

Figure 3:
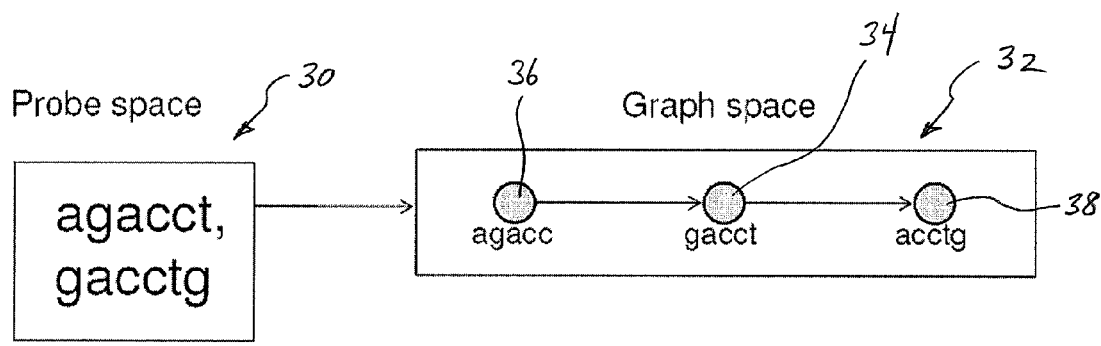
FIG. 3 is a schematic diagram of a spectrum and a graph space of a biomolecule, according to an illustrative embodiment of the invention.

When a spectrum includes more than one k-mer, the probes that share a k-1-mer prefix or suffix share the same node in graph space. For example, referring to FIG. 3, when a spectrum 30 consists of the two probes "agacct" and "gacctg," the prefix of one probe ("gacctg") is the same as the suffix of the other probe ("agacct"). In a graph space 32, the two probes share a central node 34 having the common k-1-mer portion (i.e., "gacct"), and a first end node 36 and a second end node 38 represent the remaining prefix and suffix of the two probes (i.e., "agacc" and "acctg").

Figure 4:
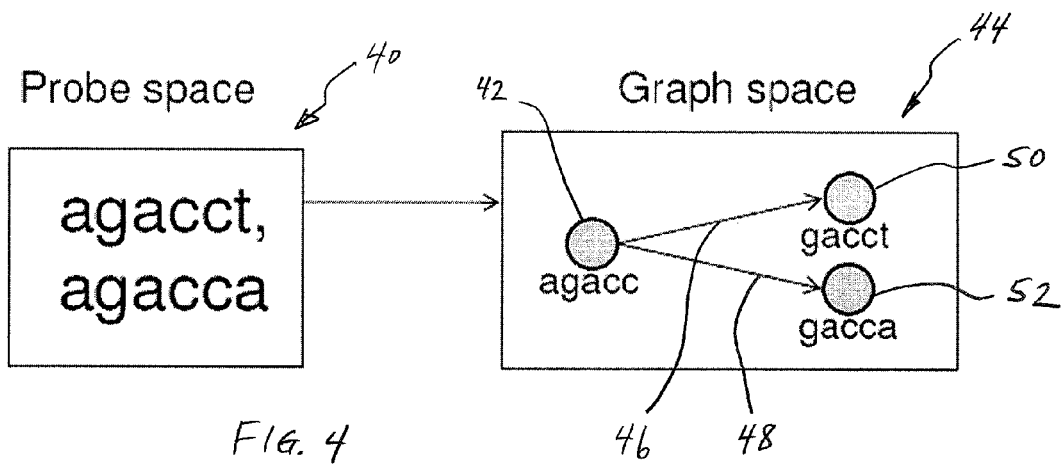
FIG. 4 is a schematic diagram of a spectrum and a graph space of a biomolecule, according to an illustrative embodiment of the invention.

Similarly, referring to FIG. 4, when a spectrum 40 consists of the two probes "agacct" and "agacca," the probes share a proximal node 42 having the common k-1-mer prefix (i.e., "agacc"). A graph space 44 in this case also includes a first branch 46 and a second branch 48 that lead to a first distal node 50 and a second distal node 52, respectively. Distal nodes 50, 52 include the suffix portions of the two probes (i.e., "gacct" and "gacca").

Figure 5:
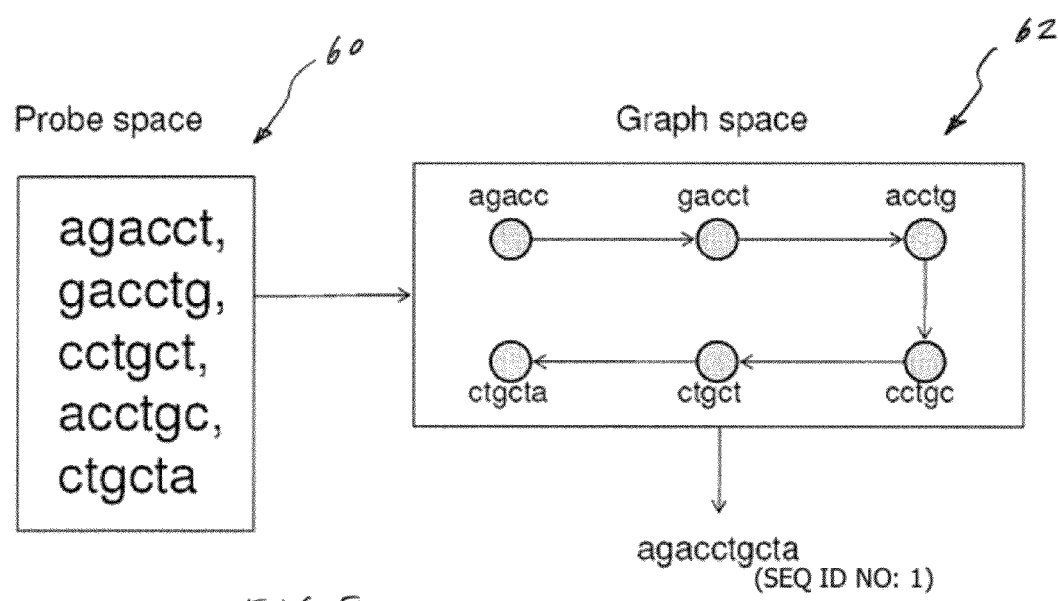
FIG. 5 is a schematic diagram of a spectrum and a graph space of a biomolecule, according to an illustrative embodiment of the invention.

Referring to FIG. 5, when a spectrum 60 includes multiple probes, the sequence of the string may be determined by arranging the probes in a graph space 62 according to a shortest common superstring (i.e., an arrangement of the probes in graph space that uses the fewest number of nodes). As depicted, when the spectrum 60 consists of "agacct," "gacctg," "cctgct," "acctgc," and "ctgcta," the arrangement in the graph space 62 reveals that the sequence of the superstring is "agacctgcta" (SEQ ID NO: 1).

Figure 6:
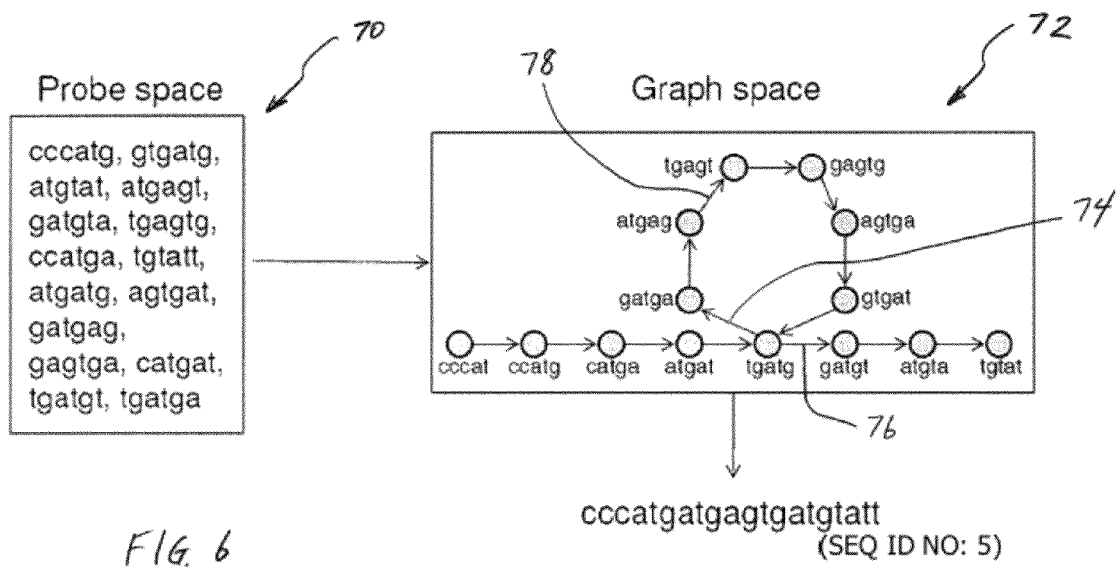
FIG. 6 is a schematic diagram of a spectrum and a graph space of a biomolecule, according to an illustrative embodiment of the invention.

As mentioned, depending on the spectrum, the graph space may include one or more branches where the sequence could proceed in two or more possible directions. These branches introduce ambiguities that may make it difficult to determine the sequence of the string because it may be unclear which branch comes first. For example, referring to FIG. 6, where a spectrum 70 consists of "cccatg," "gtgatg," "atgtat," "atgagt," "gatgta," "tgagtg," "ccatga," "tgtatt," "atgatg," "agtgat," "gatgag," "gagtga," "catgat," "tgatgt," and "tgatga," a graph space 72 includes a first branch 74 and a second branch 76 at node "tgatg," shared by probes "tgatgt" and "tgatga." The first branch 74 forms an upper loop 78 that returns to node "tgatg." As depicted, the first branch 74 and the second branch 76 create an ambiguity in which there are two possible paths to take at node "tgatg." In some instances, depending on the number of branches, for example, it will be unclear which path to take first. In this case, however, by requiring the solution to include all of the probes, it becomes clear that the first branch 74 and the upper loop 78 come before the second branch 76. Thus, in some instances, despite ambiguities or branching in the graph space, it is possible to identify the correct sequence.

Figure 7:
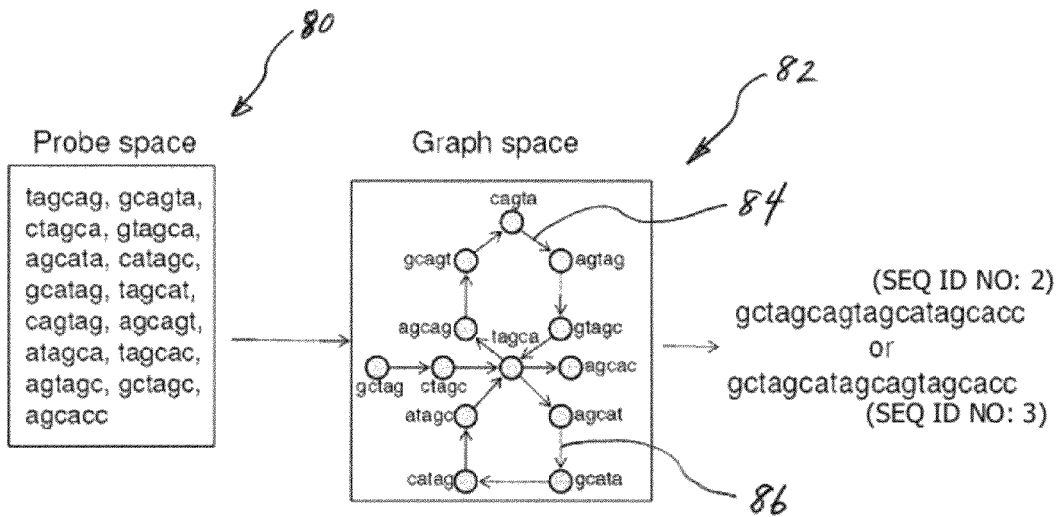
FIG. 7 is a schematic diagram of a spectrum and a graph space of a biomolecule, according to an illustrative embodiment of the invention.

For certain sequences, however, it may not be possible to recover unambiguously the correct sequence without obtaining additional information. For example, referring to FIG. 7, when a spectrum 80 consists of "tagcag," "gcagta," "ctagca," "gtagca," "agcata," "catagc," "gcatag," "tagcat," "cagtag," "agcagt," "atagca," "tagcac," "agtagc," "gctagc," and "agcacc," the above approach (i.e., requiring the solution to include all probes) leads to two possible sequences: "gctagcagtagcatagcacc" (SEQ ID NO: 2) and "gctagcatagcagtagcacc" (SEQ ID NO: 3). As depicted, a graph space 82 in this instance includes three branches at node "tagca," with three possible paths to take out of the node, and an upper loop 84 and a lower loop 86 connected to the node. Unlike the previous example, requiring the solution to use all of the probes still results in ambiguity because it remains unclear which loop comes first. Without additional information to resolve the ambiguity, the correct sequence may not be identified.

Figure 8:
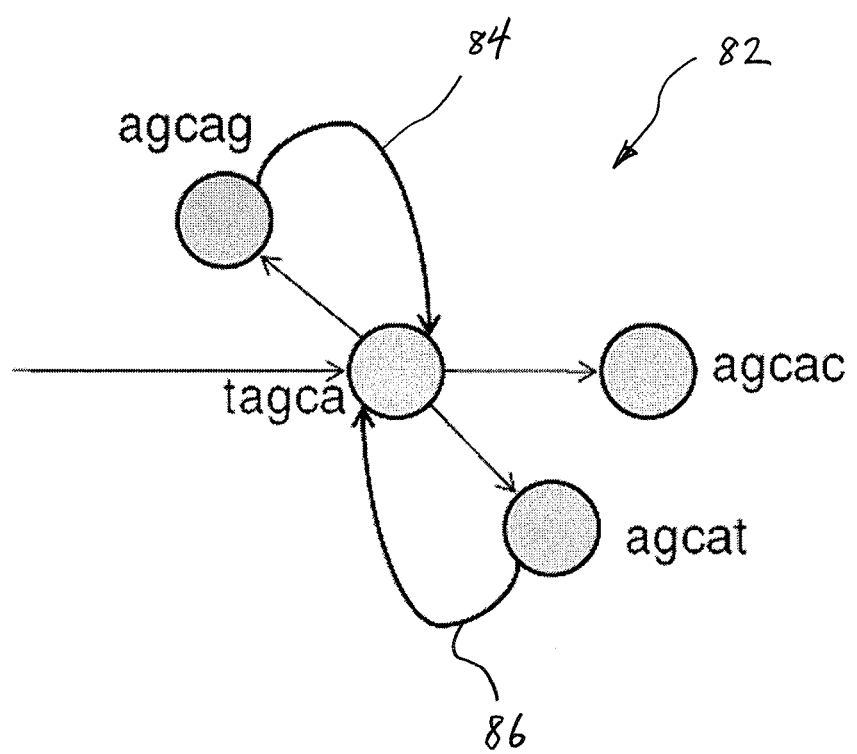
FIG. 8 is a schematic diagram of a graph space of a biomolecule, according to an illustrative embodiment of the invention.

Referring to FIG. 8, the correct sequence may be determined by identifying the correct order for the branches or loops 84, 86 at node "tagca." In other words, the only ambiguity in the graph space 82 is the relative order of the three branches or out-edges (extensions) of "tagca." In this case, requiring the solution to include all of the probes reveals that the two loops 84, 86 must come before the end node "agcag." Additional information is needed to determine which of the two loops 84, 86 comes first. In one embodiment, the relative order of branches and/or loops is determined with distinguishable tags.

As mentioned above for SBH, DNA may be sequenced by hybridizing long fragments of an unknown target with short probes of known sequence. These probes will bind to the target DNA to create binding events wherever they find their complementary sequence. The distance between these binding events may be measured, for example, by sending the target fragments and hybridized probes through a nanopore, nanochannel, micropore, or microchannel, as in Hybridization Assisted Nanopore Sequencing (HANS). For example, two reservoirs of solution are separated by a nanometer-sized hole, or nanopore, that serves as a fluidic constriction of known dimensions. The application of a constant DC voltage between the two reservoirs results in a baseline ionic current that is measured. If an analyte is introduced into a reservoir, it may pass through the fluidic channel and change the observed current, due to a difference in conductivity between the electrolyte solution and analyte. The magnitude of the change in current depends on the volume of electrolyte displaced by the analyte while it is in the fluidic channel. The duration of the current change is related to the amount of time that the analyte takes to pass through the nanopore constriction. In the case of DNA translocation through a nanopore, the physical translocation may be driven by the electrophoretic force generated by the applied DC voltage. Other driving forces, e.g., pressure, chemical potential, etc., are envisioned as well. Various micro/nano pore/channel based detection systems are described in published documents and may be used in various embodiments described herein, for example, U.S. Patent Application Publication No. US2007/0190542,, "Hybridization Assisted Nanopore Sequencing"; U.S. Patent Application Publication No. US2009/0099786,, "Biopolymer Sequencing by Hybridization of Probes to Form Ternary Complexes and Variable Range Alignment"; U.S. Patent Application Publication No. US2010/0096268,, "Use of Longitudinally Displaced Nanoscale Electrodes for Voltage Sensing of Biomolecules and Other Analytes in Fluidic Channels"; U.S. Patent Application Publication No. US2010/0243449,, "Devices and Methods for Analyzing Biomolecules and Probes Bound Thereto"; U.S. Patent Application Publication No. US2010/0261285,, "Tagged-Fragment Map Assembly"; and U.S. Patent Application Publication No. US2010/0078325,, "Devices and Methods for Determining the Length of Biopolymers and Distances Between Probes Bound Thereto," the texts of which are all incorporated herein by reference in their entirety. The methods, apparatus, and systems of the following pending patent applications may also be used in various embodiments described herein: U.S. Patent Application Publication No. 2010/0310421,, "Devices and Methods for Analyzing Biomolecules and Probes Bound Thereto," by Oliver et al.; and U.S. patent application Ser. No. 12/891,343,, "Assay Methods Using Nicking Endonucleases," by Oliver, the texts of which are all incorporated herein by reference in their entirety.

As the target and probe travel through the nanopore, current or voltage readings across the nanopore allow the unlabeled or unhybridized backbone of the target DNA to be distinguished from hybridized points on the backbone that are binding sites for probes. Since DNA translocates at an approximately constant velocity through a nanopore, a time course or time history of such current or voltage measurements provides a measurement of the distance between probe binding sites on the target DNA.

Figure 9:
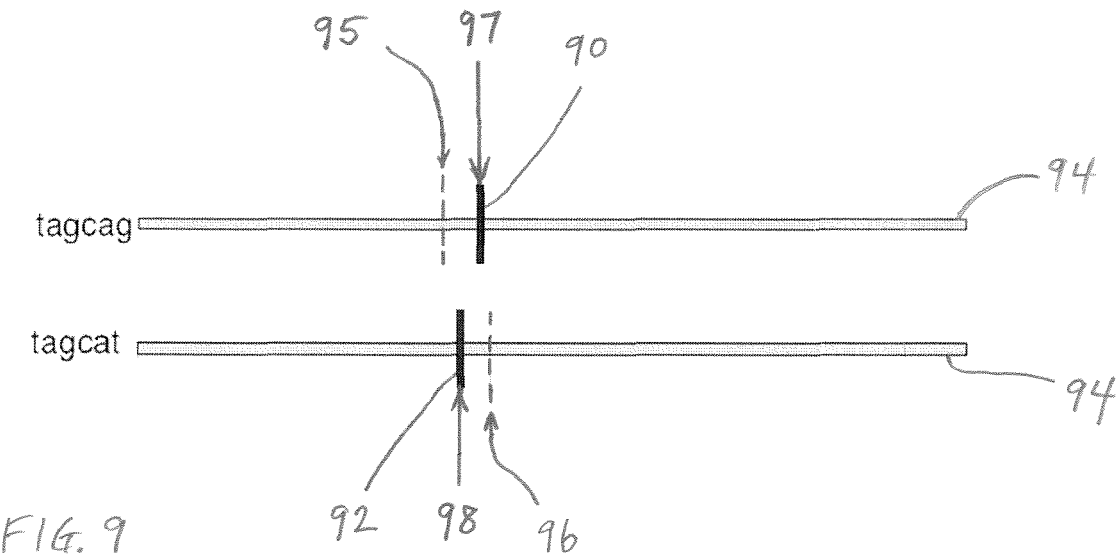
FIG. 9 is a schematic diagram of probes that have hybridized to two separate biomolecules, according to an illustrative embodiment of the invention.

Referring to FIG. 9, a first probe 90 (e.g., "tagcag") and a second probe 92 (e.g., "tagcat") may be hybridized separately to two identical target biomolecules 94. In the depicted embodiment, the first probe 90 is hybridized at a first actual position 95, and the second probe 92 is hybridized at a second actual position 96. A measured absolute position 97 of the first probe 90 and a measured absolute position 98 of the second probe 92, along the length of the biomolecules 94, may be determined using, for example, a nanopore or other technique, described above. Due to measurement errors, however, the measured absolute positions 97, 98 may differ from the actual or true absolute positions 95, 96, and this may lead to an incorrect determination of the order for the two probes. As depicted, the measured positions 97, 98 in this case suggest "tagcat" comes before "tagcag," but the actual positions 95, 96 indicate the opposite ordering (i.e., that "tagcag" comes before "tagcat").

To avoid these errors, it is desirable to measure directly the relative positions of the two probes. In one embodiment, the relative positions are revealed with the use of distinguishable tags.

Distinguishable tagging refers to attaching tags to the probes so that each probe may be individually distinguished from other probes. Specifically, when a hybridized probe has been detected along a biomolecule, distinguishable tags make it possible to identify the specific probe that has been detected. For example, in the case of a reaction involving a target and two probes, A and B, without distinguishable tagging it may be difficult or impossible to tell whether a particular binding site corresponds to probe A or probe B.

Figure 10:
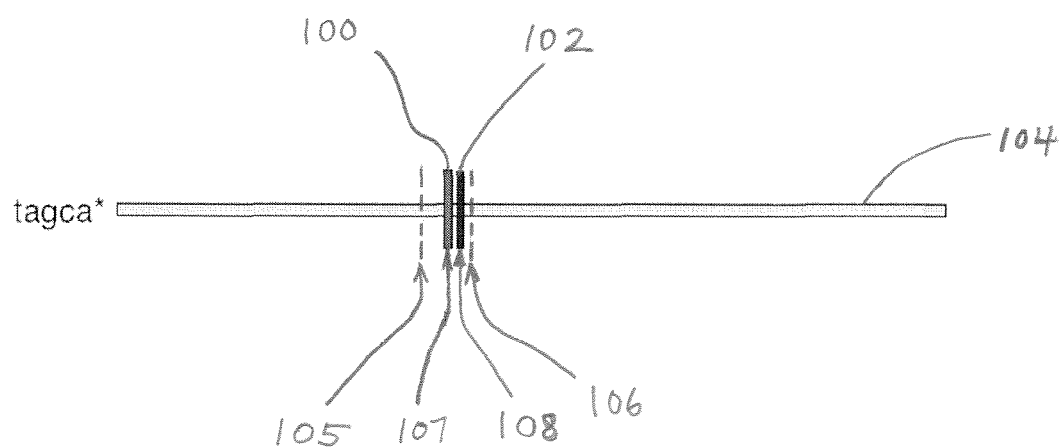
FIG. 10 is a schematic diagram of probes that have hybridized to a single biomolecule, according to an illustrative embodiment of the invention.

As explained herein in further detail, it is advantageous to pool different probes together in particular ways, meaning that a single hybridization reaction includes the target and not one but multiple probes having different, known sequences. Referring to FIG. 10, a first probe and tag combination 100 and a second probe and tag combination 102 (e.g., "tagcag" and "tagcat," each with a distinguishable tag) may be pooled together and hybridized to a single biomolecule 104. In the depicted embodiment, the first combination 100 is hybridized at a first actual position 105 and the second combination 102 is hybridized at a second actual position 106. Using a detection system, such as a nano/micro pore or channel-based system, a measured first absolute position 107 of the first combination 100 and a measured second position 108 of the second combination 102, along the biomolecule 104, may be determined. As in a non-pooled, single probe hybridization test, measures of absolute position will contain errors and the measured absolute positions 107, 108 may differ from the actual absolute positions 105, 106, resulting in sequencing error. However, where distinguishable tags are attached to pooled probes, the tags allow the probes to be uniquely identified, and as the biomolecule linearly translocates through or past the device, the specific probes are identified and the correct order of the probes is revealed, since each probe is detected in the order in which it is attached or hybridized. Determination of the relative occurrence of sequential electrical signals representing the different probes and the non-hybridized molecule backbone is much less prone to error than determination of absolute position. Using this technique, the relative positions of all probes in the spectrum may be directly measured. By pooling probes in the manner described in more detail herein below, it is possible to avoid ambiguities, such as the branches and/or loops, described above, that may lead to erroneous biomolecule sequencing.

Figure 11:
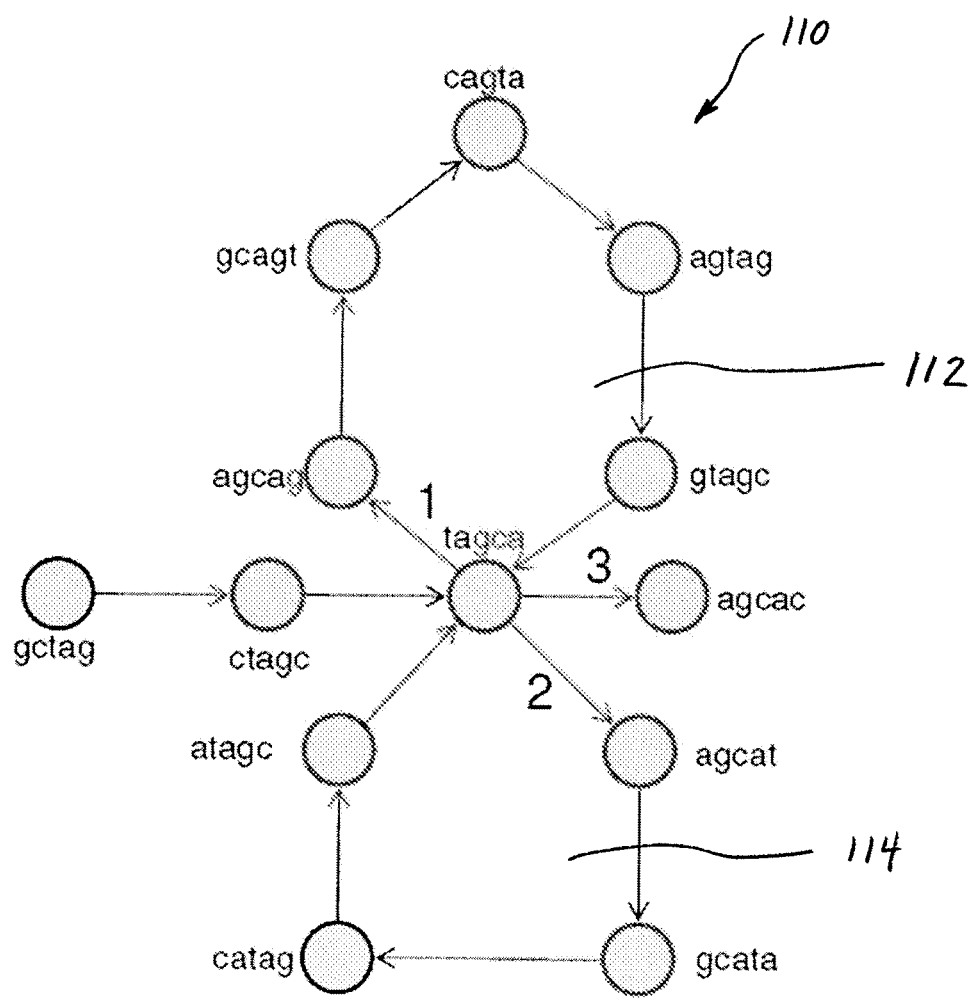
FIG. 11 is a schematic diagram of a graph space of a biomolecule, according to an illustrative embodiment of the invention.

Reconstruction is significantly simplified by pooling and tagging in this way. For example, with SBH, any sufficiently long sequence is ambiguous because of repeat ambiguities. Similarly, with previous Hybridization-Assisted Nanopore Sequencing (HANS) techniques, the reconstruction in graph space may need to be branched extensively in order to gather enough data to make a statistically meaningful choice. With the distinguishable tagging approach, however, sequencing may proceed without branching. Referring to FIG. 11, the relative order information informs the precise path to take through a graph space 110 so that ambiguities are resolved and no search or statistical scoring is needed. For example, in the depicted embodiment, by determining the correct relative order of hybridized probes, it is revealed that an upper loop 112 comes before a lower loop 114.

As mentioned, when probes are tagged in a distinguishable fashion, a specific probe can be identified for each binding site. In addition to eliminating the ambiguity introduced by pooling, such tagging can be helpful for specific aspects of a sequence reconstruction algorithm. For example, the presence of four distinguishable tags enables an extension to sequencing by hybridization, herein referred to as Distinguishable-Tagging Sequencing by Hybridization (dtSBH).

Solving traditional SBH involves finding an Eulerian path (a path that traverses all edges or nodes) through the graph space representing the spectrum of detected k-mers. The limitations to SBH come from the fact that any sufficiently dense graph with one solution has multiple equally well-supported solutions. These multiple solutions may be distinguished, however, by determining the relative order of edges (i.e., nodes) out of each vertex (i.e., a node having branches) in the graph.

In certain embodiments, with dtSBH, to provide the relative order of all paths out of each k-1-length sequence, probes are pooled together in groups of four and tagged with distinguishable tags. Specifically, for each of the $4^{k-1}$, possible k-1-length sequences of DNA, a pool of the four k-mer extensions of this k-1-mer is formed. (For example, when k=6, and the k-1-length sequence is "agacc," the pool consists of "agacca," "agaccc," "agaccg" and "agacct.") Each k-mer probe in the pool is then tagged with a distinguishable tag such that it is possible to associate a specific probe with a detected probe-binding event. In certain embodiments, the pool of four probes is subdivided into combinations of two or three of the four probes at a time. The same sequencing information may be obtained in this manner, for example, by performing six reactions of pairwise-distinguished probes, or by performing four reactions of three probes at a time.

When using nanopore detection, DNA translocates through the nanopore in a linear fashion. For example, if a given target fragment has probe-binding events ($p_1, p_2, \ldots, p_n$), these events will always be detected in order ($p_1, p_2, \ldots, p_n$) or, when the target translocates in a backwards direction, in the reverse order ($p_n, p_{n-1}, p_{n-2}, \ldots, p_1$). As a result, a properly assembled probe-binding event map includes a complete ordering of all edges out of a particular k-1-mer vertex or node in the graph space. By constructing the path uniquely defined by following the edges out of vertices in the specified order, the target nucleic acid sequence may be recovered correctly without search or ambiguity.

Figure 12:
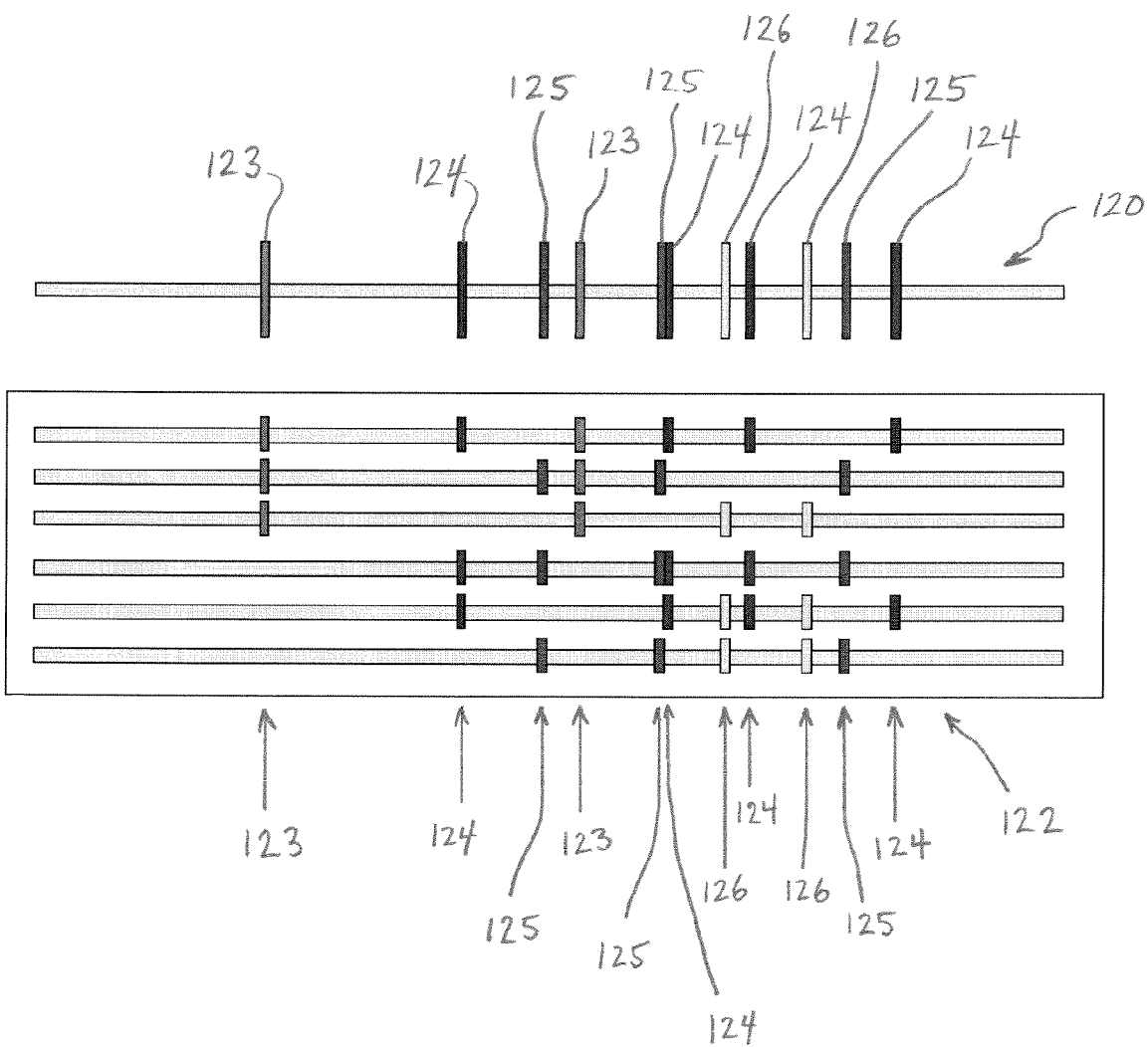
FIG. 12 is a schematic diagram of probes hybridized to biomolecules, according to an illustrative embodiment of the invention.

While the description above has relied on four distinguishable tags, the same information can be gathered with the use of only two physically distinct probe-tagging chemical groups. As shown in FIG. 12, a single reaction 120 of four pooled probes may be divided into six reactions 122 of pairwise-distinguished probes. For example, in the single reaction 120, a first tagged probe 123, a second tagged probe 124, a third tagged probe 125, and a fourth tagged probe 126 are hybridized to the same biomolecule. By comparison, in the six reactions 122, each reaction includes one of the six possible combinations of the four types of tagged probes 123, 124, 125, 126. Because the relative order of each pair of consecutive probes is captured in the six-pool (two-probe) case, these relative orders may be assembled to obtain the same information that is obtainable in the four-probe (one-pool) case. This point is made to emphasize that only two electrically distinguishable chemical groups or tags need to be identified in order to gather the information needed to reconstruct nucleotide sequences of arbitrary length with no ambiguity.

In certain embodiments, rather than using four or two distinct tags, the relative positions of four probes in a given pool may be determined using three distinct tags attached to three of the four probes in the pool at a time, where the nano/micro pore/channel detection system can electrically distinguish between the three different tags. There are four combinations of three-member groups of the four probes. Thus, four separate reactions are run, with each reaction including one of the four possible three-probe combinations of the four probes in the pool. For example, the four different three-probe combinations of the pool of probes A, B, C, and D are as follows: (A, B, C); (A, C, D); (A, B, D); and (B, C, D). For each reaction, the relative positions of the three probes are determined, and the information from the four reactions is assembled to obtain the same information (i.e., the relative positions of the four probes) that is obtainable in the one-pool (four distinguishable tags) case or the six-pool (two distinguishable tags) case.

Examples of electrically distinguishable tags which may be used in various embodiments discussed herein include proteins, double-stranded DNA, single-stranded DNA, fragments thereof, or other molecules. In some embodiments, tags may include dendrimers, beads, or peptides. When used with nano/micro pore/channel detectors, tags may have either a larger volume than the probe or a different charge so that they slow translocation of the biomolecule through the nanopore or fluidic channel. In certain embodiments, optically distinguishable tags may be used (e.g., fluorescent labels).

Figure 13:
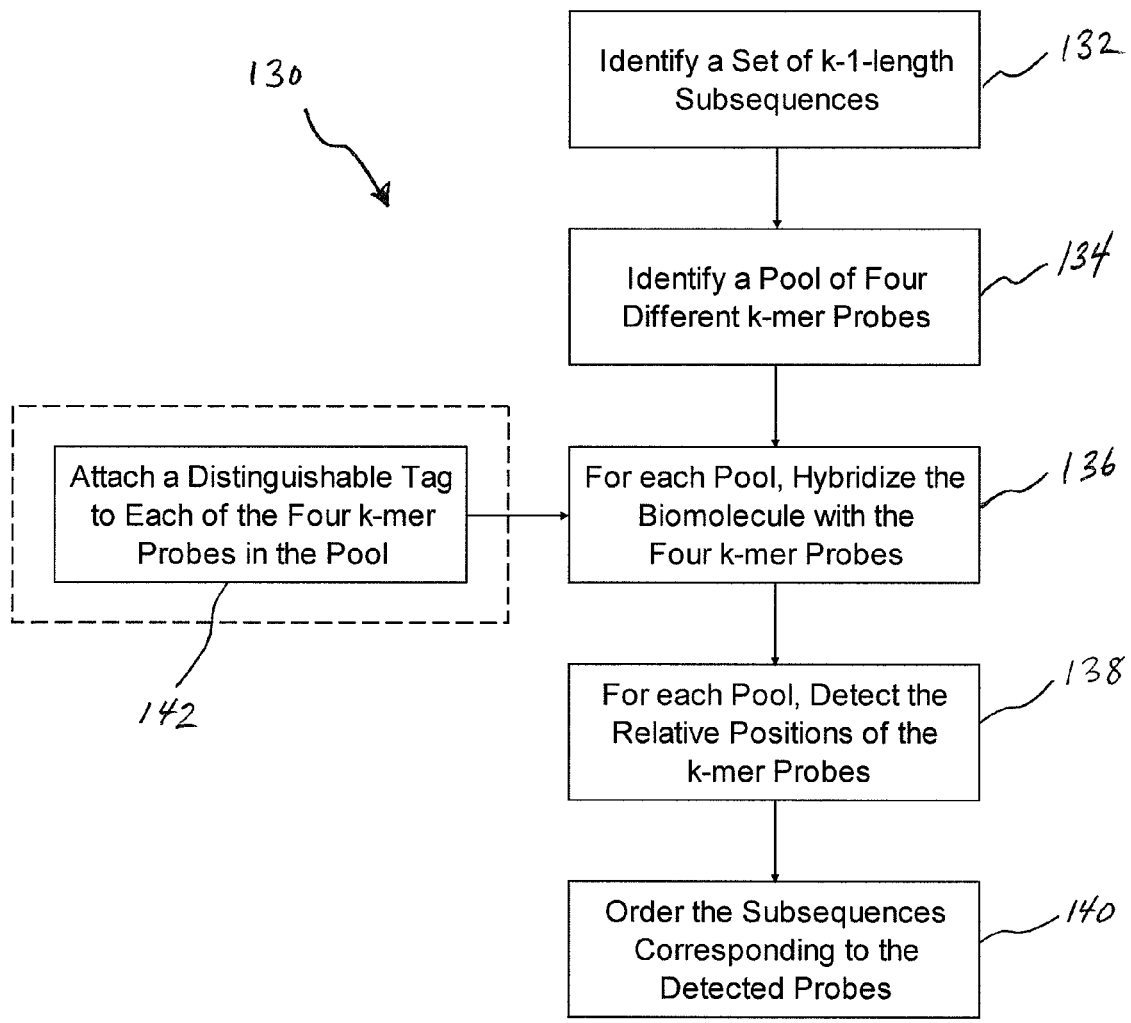
FIG. 13 is a flowchart depicting a method for sequencing a biomolecule, according to an illustrative embodiment of the invention.

FIG. 13 is a flowchart depicting an embodiment of a method 130 for determining the sequence of a biomolecule. As depicted, a set of k-1-length subsequences is identified (step 132) that represents a plurality of substrings of a sequence string s of the biomolecule. For each of the k-1-length subsequences, a pool is identified (step 134) that consists of the four different k-mer extensions of the k-1-length subsequence. For each identified pool: (i) the biomolecule is hybridized (step 136) with the four k-mer probes making up the pool, and (ii) relative positions of the hybridized k-mer probes are detected (step 138). Given these relative positions, the subsequences corresponding to the detected attached probes are ordered (step 140) to determine the sequence string s of the biomolecule. In certain embodiments, a distinguishable tag is attached (step 142) to each of the four k-mer probes in each identified pool.

In certain embodiments, to get around the fundamental limitations of SBH, the absolute positions of hybridized probes along a biomolecule may be measured using, for example, a nanopore. The absolute positional information provides statistical power to determine the correct relative order of extensions (i.e., the path through graph space) at a vertex or branch in graph space.

Figure 14:
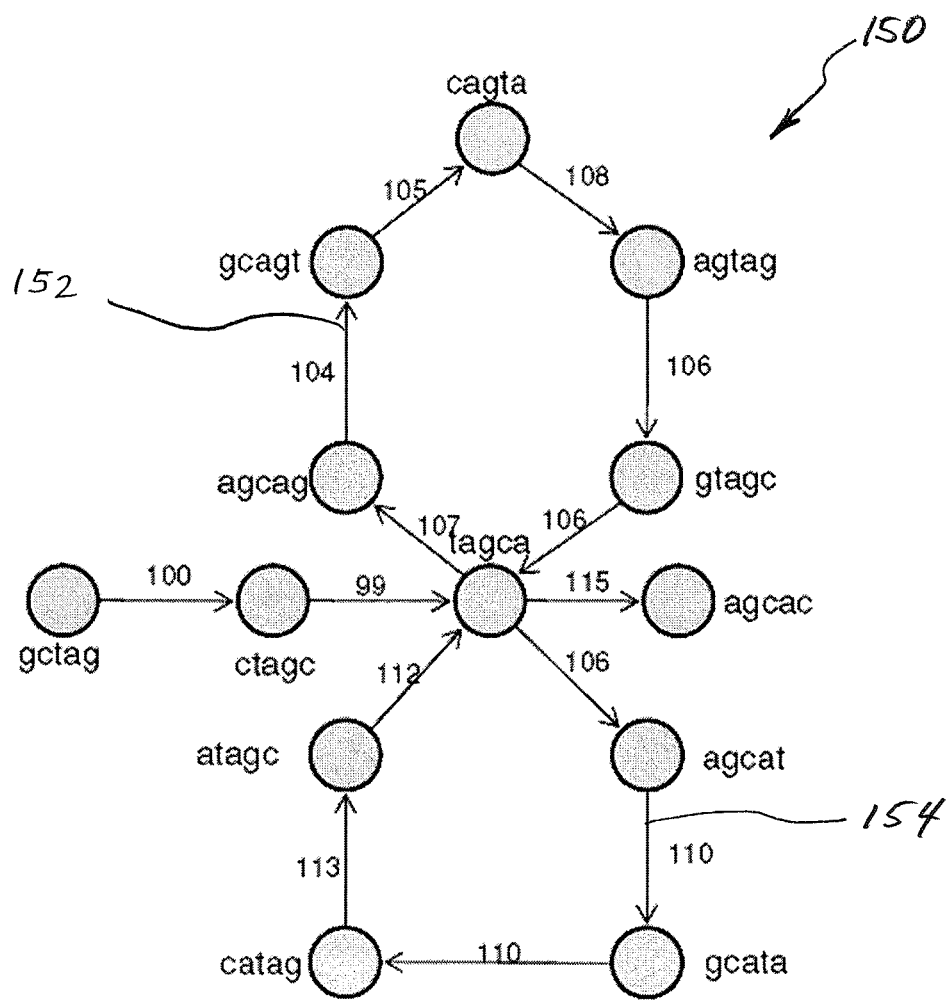
FIG. 14 is a schematic diagram of a graph space of a biomolecule, according to an illustrative embodiment of the invention.

As discussed above, SBH ambiguities (i.e., branches and/or loops) may be resolved by determining the relative positions of hybridized probes. Referring to FIG. 14, a graph space 150 may include an ambiguity with an upper loop 152 and a lower loop 154. In this case, to determine the correct sequence of the biomolecule, it is necessary to determine which loop comes first along the path through the graph space 150. In one embodiment, the order of the loops is determined by measuring the absolute positions of the hybridized probes in each loop.

FIG. 14 depicts measured absolute positions for each probe in the spectrum. Note that the measured absolute positions of probes "tagcag" and "tagcat" (i.e., the two probes at the beginning of each loop) are 107 and 106, respectively. The lower measured absolute position of "tagcat" suggests that the lower loop 154 comes before the upper loop 156. Due to measurement errors, however, this may be incorrect. As discussed below, rather than considering only the first probe in each loop, a more accurate determination of the order of the loops may be obtained by averaging the measured absolute positions of two or more probes in each of the loops.

Figure 15:
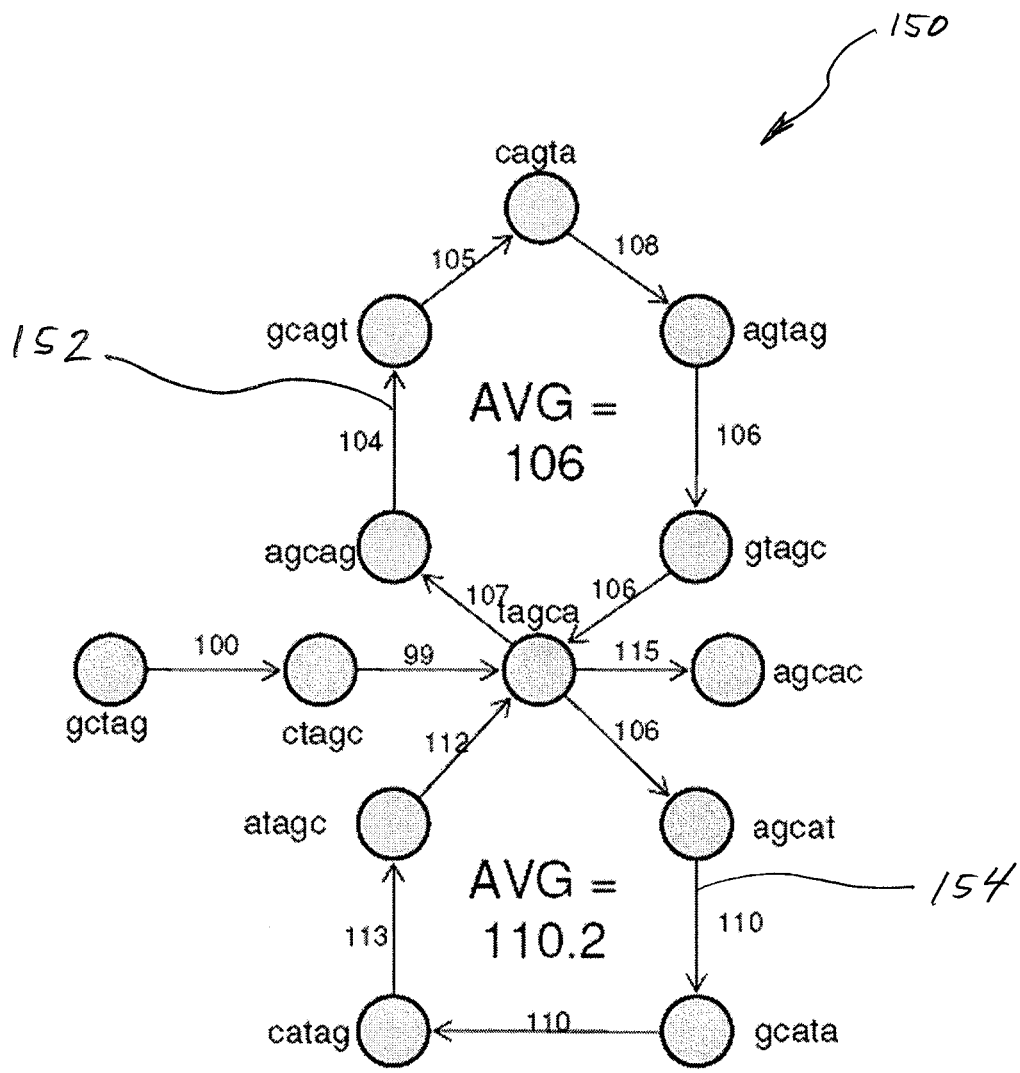
FIG. 15 is a schematic diagram of a graph space of a biomolecule, according to an illustrative embodiment of the invention.

For example, referring to FIG. 15, the averages of the measured absolute positions of the probes in the top loop 152 and the bottom loop 154 are 106 and 110.2, respectively. The lower average position for the top loop 152 indicates that the top loop 152 comes before the bottom loop 154, which is true in this case. Thus, by averaging the measured absolute positions within the two loops, the proper order of the loops is more accurately revealed than by simply measuring the absolute positions of the first probe at the beginning of each loop (i.e., "tagcag" and "tagcat" in this case). Due to measurement errors and the probabalistic nature of this averaging approach, however, the identified order may still be uncertain, particularly if there are only a few probes in each branch (loop).

Figure 16:
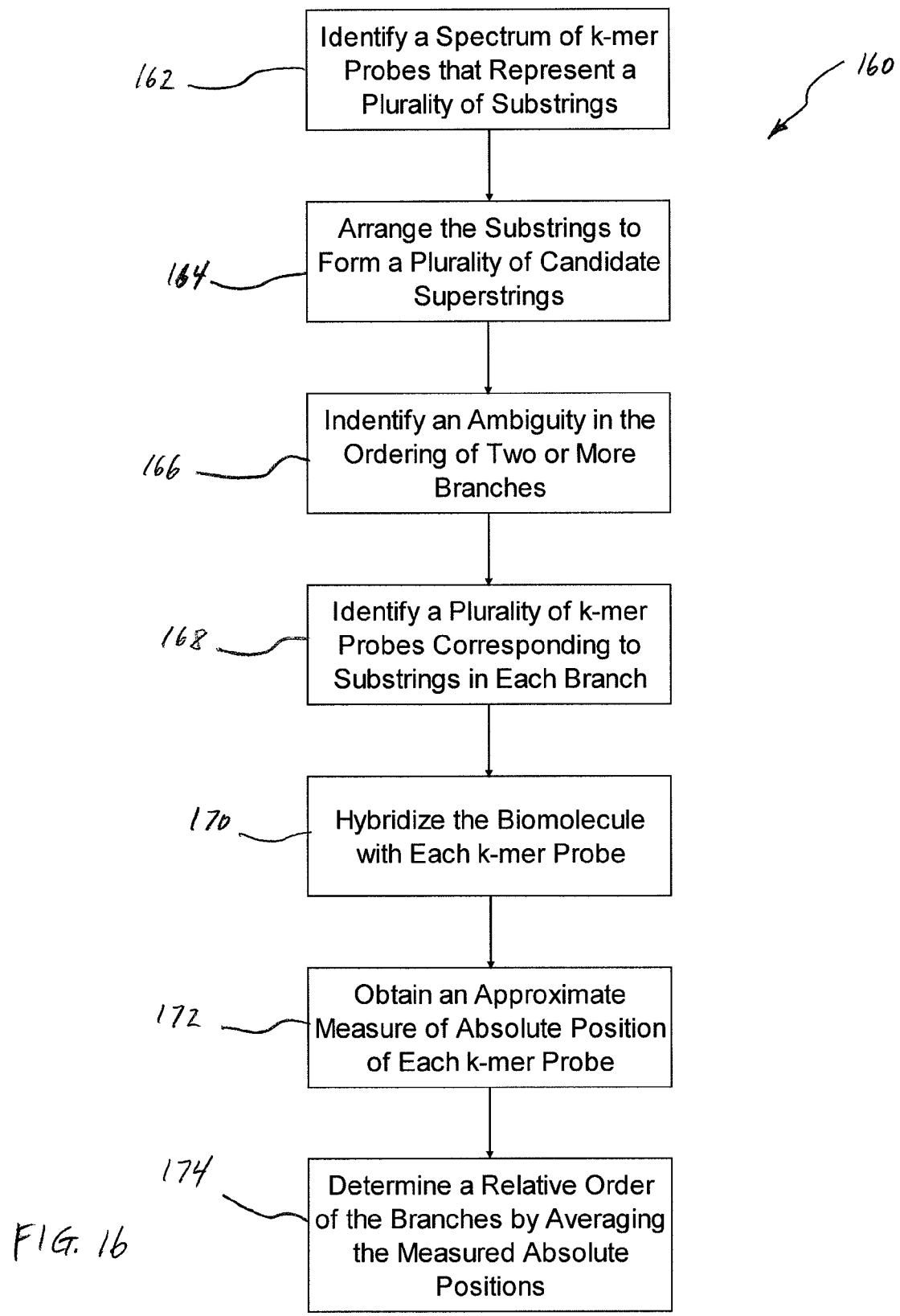
FIG. 16 is a flowchart depicting a method for sequencing a biomolecule, according to an illustrative embodiment of the invention.

FIG. 16 is flowchart depicting an embodiment of a method 160 for determining a sequence of a biomolecule. A spectrum of k-mer probes is identified (step 162) that represents a plurality of substrings of a sequence string s of the biomolecule. The substrings are arranged (step 164) to form a plurality of candidate superstrings, with each candidate containing all the identified substrings. Each candidate superstring has a length corresponding to the shortest possible arrangement of all the substrings. An ambiguity is identified (step 166) in the ordering of two or more branches or loops common to the candidate superstrings. A plurality of k-mer probes is identified (step 168) that corresponds to the substrings along each of the two or more branches. For each k-mer probe that has been identified, the biomolecule is hybridized (step 170) with the k-mer probe. An approximate measure is obtained (step 172) for the absolute position of the k-mer probe along the biomolecule. For each branch, a relative order is determined (step 174) by (i) obtaining an average of the measures of absolute position of each k-mer probe (identified in step 168) that is in the branch, and (ii) ordering the two or more branches according to the average absolute position measures identified for each branch. With the branches in the proper order, the ambiguities have been resolved and the sequence string s of the biomolecule may be identified correctly. In certain embodiments, rather than averaging the measured absolute positions of all probes in a given branch, the method includes averaging the measured absolute positions of only a portion (i.e., two or more) of the probes in the branch.

Figure 17:
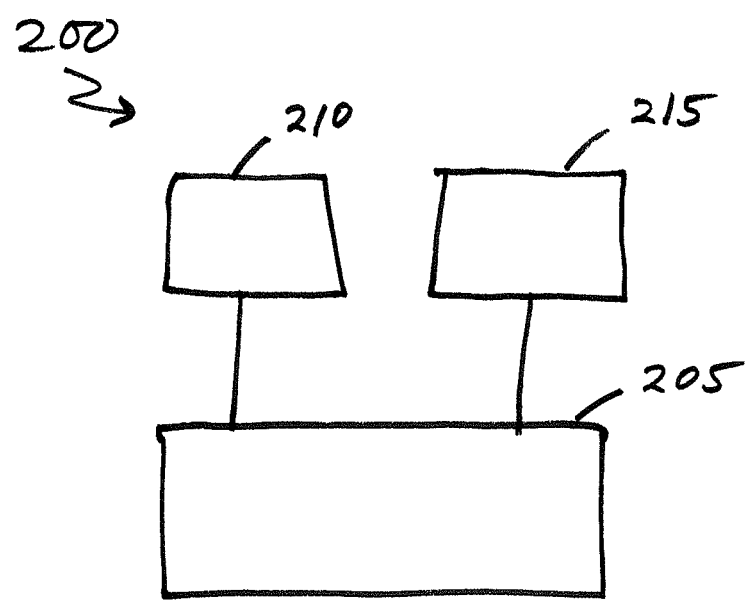
FIG. 17 is a schematic drawing of a computer and associated input/output devices, according to an illustrative embodiment of the invention

FIG. 17 is a schematic drawing 200 of a computer and associated input/output devices, per certain embodiments of the invention. The computer 205 in FIG. 17 can be a general purpose computer, such as a commercially available personal computer that includes a CPU, one or more memories, one or more storage media, one or more output devices 210, such as a display, and one or more user input devices 215, such as a keyboard. The computer operates using any commercially available operating system, such as any version of the Windows™ operating systems from Microsoft Corporation of Redmond, Wash., or the Linux™ operating system from Red Hat Software of Research Triangle Park, N.C. The computer is programmed with software including commands that, when operating via a processor, direct the computer in the performance of the methods of the invention. Those of skill in the programming arts will recognize that some or all of the commands can be provided in the form of software, in the form of programmable hardware such as flash memory, ROM, or programmable gate arrays (PGAs), in the form of hard-wired circuitry, or in some combination of two or more of software, programmed hardware, or hard-wired circuitry.

Commands that control the operation of a computer are often grouped into units that perform a particular action, such as receiving information, processing information or data, and providing information to a user. Such a unit can comprise any number of instructions, from a single command, such as a single machine language instruction, to a plurality of commands, such as a plurality of lines of code written in a higher level programming language such as C++. Such units of commands are referred to generally as modules, whether the commands include software, programmed hardware, hard-wired circuitry, or a combination thereof. The computer and/or the software includes modules that accept input from input devices, that provide output signals to output devices, and that maintain the orderly operation of the computer. In certain embodiments, the computer 205 is a laptop computer, a mini-computer, a mainframe computer, an embedded computer, or a handheld computer. The memory is any conventional memory such as, but not limited to, semiconductor memory, optical memory, or magnetic memory. The storage medium is any conventional machine-readable storage medium such as, but not limited to, floppy disk, hard disk, CD-ROM, and/or magnetic tape. The one or more output devices 210 may include a display, which can be any conventional display such as, but not limited to, a video monitor, a printer, a speaker, and/or an alphanumeric display. The one or more input devices 215 may include any conventional input device such as, but not limited to, a keyboard, a mouse, a touch screen, a microphone, and/or a remote control. The computer 205 can be a stand-alone computer or interconnected with at least one other computer by way of a network. This may be an internet connection.

In certain embodiments, the computer 205 in FIG. 17 includes and/or runs software for determining a sequence of a biomolecule (e.g., DNA) from input data, e.g., data from HANS and/or SBH experiments, according to the methods described herein. In certain embodiments, one or more modules of the software may be run on a remote server, e.g., the user may access and run the software via the internet.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for determining a sequence of a biomolecule, the method comprising the steps of:
   (a) identifying a spectrum of k-mer probes that represent a plurality of substrings of a sequence string s of the biomolecule;
   (b) arranging the substrings to form a plurality of candidate superstrings each containing all the substrings in step (a), wherein each candidate superstring has a length corresponding to the shortest possible arrangement of all the substrings;
   (c) identifying an ambiguity in the ordering of two or more branches common to the candidate superstrings and identifying a plurality of k-mer probes corresponding to the substrings along each of the two or more branches;
   (d) for each k-mer probe identified in step (c), hybridizing the biomolecule with the k-mer probe and obtaining an approximate measure of absolute position of the k-mer probe along the biomolecule;
   (e) determining a relative order of the two or more branches by, for each branch, obtaining an average of the measures of absolute position of each k-mer probe identified in step (c) that are in the branch, and ordering the two or more branches according to the average absolute position measures identified for each branch, thereby identifying the sequence string s of the biomolecule.

2. The method of claim 1, wherein steps (a) and (d) are performed simultaneously.

3. The method of claim 1, wherein steps (a) and (d) are performed using HANS.

4. The method of claim 1, wherein step (a) is performed using SBH.

5. The method of claim 1, wherein step (d) comprises monitoring an electrical signal across a fluidic channel or pore or within a fluidic volume of a channel or pore as the hybridized biomolecule translocates therethrough, the electrical signal being indicative of hybridized portions of the biomolecule and non-hybridized portions of the biomolecule.

6. The method of claim 1, wherein the spectrum of k-mer probes represents a complete set of substrings of the sequence strings.

* * * * *